US009861265B2

(12) United States Patent
Yamaoka

(10) Patent No.: US 9,861,265 B2
(45) Date of Patent: Jan. 9, 2018

(54) PNEUMOPERITONEUM APPARATUS

(71) Applicant: OLYMPUS CORPORATION, Hachioji-shi, Tokyo (JP)

(72) Inventor: Koji Yamaoka, Hamura (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/163,057

(22) Filed: May 24, 2016

(65) Prior Publication Data
US 2016/0262600 A1 Sep. 15, 2016

Related U.S. Application Data

(63) Continuation of application No. PCT/JP2014/076676, filed on Oct. 6, 2014.

(30) Foreign Application Priority Data

Dec. 26, 2013 (JP) .................. 2013-269993

(51) Int. Cl.
*A61M 13/00* (2006.01)
*A61B 1/015* (2006.01)

(52) U.S. Cl.
CPC .............. *A61B 1/015* (2013.01); *A61M 13/00* (2013.01); *A61M 13/003* (2013.01);
(Continued)

(58) Field of Classification Search
CPC .......... A61B 1/01; A61B 1/015; A61M 13/00; A61M 2205/3331; A61M 2205/3337
See application file for complete search history.

(56) References Cited

U.S. PATENT DOCUMENTS 2,169,324 A * 8/1939 Monnot ................. A61C 17/14
   4/263
2,771,072 A * 11/1956 De Montauge ..... A61M 1/0084
   604/41
(Continued)

FOREIGN PATENT DOCUMENTS

EP    1825802 A1   8/2007
JP    S61-48332 A  3/1986
(Continued)

OTHER PUBLICATIONS

Jun. 28, 2016 International Preliminary Report on Patentability issued in International Patent Application No. PCT/JP2014/076676.
(Continued)

*Primary Examiner* — Imani Hayman
*Assistant Examiner* — Matthew A Engel
(74) *Attorney, Agent, or Firm* — Oliff PLC

(57) ABSTRACT

A pneumoperitoneum apparatus includes: an insufflation conduit for pneumoperitoneum; an endoscope connection tube connecting the insufflation conduit for pneumoperitoneum; an insufflation flow rate measuring section that measures an insufflation flow rate as a measured flow rate; a set flow rate setting section that sets the measured insufflation flow rate to a target set flow rate; an insufflation flow rate adjusting section; an adjustment value storing section that if the measured flow rate is equal to the target set flow rate, stores the adjustment value for the insufflation flow rate adjusting section; and a control section that if the measured flow rate varies to a value that is equal to or below a threshold value after the measured flow rate reaches the target set flow rate, performs control to set the adjustment value read from the adjustment value storing section for the insufflation flow rate adjusting section.

13 Claims, 17 Drawing Sheets

(52) U.S. Cl.
CPC .............. *A61M 2202/0225* (2013.01); *A61M 2205/3331* (2013.01); *A61M 2205/3334* (2013.01); *A61M 2205/50* (2013.01); *A61M 2205/502* (2013.01)

(56) References Cited

U.S. PATENT DOCUMENTS

| | | | | |
|---|---|---|---|---|
| 3,508,546 A * | 4/1970 | Christie | ............. | A61M 3/0258 417/411 |
| 4,184,510 A * | 1/1980 | Murry | ................ | A61F 9/00745 137/512 |
| 4,490,331 A * | 12/1984 | Steg, Jr. | ............... | A61M 1/1698 128/DIG. 3 |
| 4,519,385 A * | 5/1985 | Atkinson | ............ | A61M 1/0064 601/161 |
| 4,561,431 A * | 12/1985 | Atkinson | ............ | A61M 3/0258 601/161 |
| 4,599,093 A * | 7/1986 | Steg, Jr. | ............... | A61M 1/3632 210/188 |
| 4,655,197 A * | 4/1987 | Atkinson | ............ | A61M 1/0058 601/160 |
| 4,669,453 A * | 6/1987 | Atkinson | ............ | A61M 1/0058 433/80 |
| 4,676,774 A | 6/1987 | Semm et al. | | |
| 4,715,372 A * | 12/1987 | Philippbar | ..... | A61B 17/320016 606/10 |
| 4,803,992 A * | 2/1989 | Lemelson | .......... | A61B 1/00096 600/342 |
| 5,046,486 A * | 9/1991 | Grulke | ................ | A61C 17/028 601/161 |
| 5,152,745 A * | 10/1992 | Steiner | ................ | A61M 13/003 141/197 |
| 5,152,746 A * | 10/1992 | Atkinson | ............ | A61M 3/0258 604/245 |
| 5,328,458 A * | 7/1994 | Sekino | ................ | A61M 13/003 604/23 |
| 5,360,396 A * | 11/1994 | Chan | ................... | A61M 13/003 600/560 |
| 5,373,317 A * | 12/1994 | Salvati | ............... | A61B 1/00052 348/65 |
| 5,423,741 A * | 6/1995 | Frank | ................. | A61M 13/003 604/23 |
| 5,439,441 A * | 8/1995 | Grimsley | ............ | A61M 13/003 600/561 |
| 5,470,305 A * | 11/1995 | Arnett | ................. | A61M 3/0258 433/80 |
| 5,476,447 A * | 12/1995 | Noda | ................. | A61B 18/1482 604/26 |
| 5,531,680 A * | 7/1996 | Dumas | ................ | A61M 5/142 417/474 |
| 5,632,761 A * | 5/1997 | Smith | ................. | A61B 1/00082 600/207 |
| 5,647,852 A * | 7/1997 | Atkinson | ............ | A61M 1/0058 417/360 |
| 5,697,364 A * | 12/1997 | Chua | ..................... | A61M 16/00 128/204.18 |
| 5,840,016 A * | 11/1998 | Kitano | ..................... | A61B 1/12 251/335.2 |
| 5,879,289 A * | 3/1999 | Yarush | ................ | A61B 1/00039 600/109 |
| 5,897,525 A * | 4/1999 | Dey | ..................... | A61M 13/003 604/65 |
| 5,993,378 A * | 11/1999 | Lemelson | .......... | A61B 1/00096 600/109 |
| 6,021,341 A * | 2/2000 | Scibilia | ................... | G01T 1/161 600/407 |
| 6,042,573 A * | 3/2000 | Lucey | ................. | A61B 17/3423 604/23 |
| 6,077,246 A * | 6/2000 | Kullas | ................. | A61M 1/0058 417/477.2 |
| 6,210,404 B1 * | 4/2001 | Shadduck | .......... | A61B 18/1492 606/34 |
| 6,238,365 B1 * | 5/2001 | Gord | .................... | A61M 13/003 604/26 |
| 6,299,592 B1 * | 10/2001 | Zander | ................ | A61M 13/003 600/560 |
| 6,315,712 B1 * | 11/2001 | Rovegno | .......... | A61B 1/00052 348/E7.085 |
| 6,436,072 B1 * | 8/2002 | Kullas | ................. | A61M 1/0058 417/477.2 |
| 6,439,228 B1 * | 8/2002 | Hete | ..................... | A61M 16/04 128/200.26 |
| 6,497,687 B1 * | 12/2002 | Blanco | ............... | A61B 17/3494 604/164.01 |
| 6,623,445 B1 * | 9/2003 | Nelson | ................ | A61M 1/0043 604/249 |
| 6,652,453 B2 * | 11/2003 | Smith | ................ | A61B 1/00052 600/188 |
| 6,697,048 B2 * | 2/2004 | Rosenberg | ............. | G01B 5/008 345/156 |
| 6,716,201 B2 * | 4/2004 | Blanco | ................ | A61B 17/3494 604/164.01 |
| 6,719,746 B2 * | 4/2004 | Blanco | ................ | A61B 17/3494 604/164.01 |
| 6,929,600 B2 * | 8/2005 | Hill | .................... | A61B 1/00052 600/120 |
| 7,056,123 B2 * | 6/2006 | Gregorio | ............... | G09B 23/285 434/262 |
| 7,070,574 B2 * | 7/2006 | Jackson | ............ | A61B 17/00234 604/22 |
| 7,214,213 B2 * | 5/2007 | Michel | ............... | A61M 5/31553 604/207 |
| 7,404,716 B2 * | 7/2008 | Gregorio | ............... | G09B 23/285 434/262 |
| 7,413,543 B2 * | 8/2008 | Banik | ................ | A61B 1/00071 600/109 |
| 7,476,213 B2 * | 1/2009 | Uesugi | ................ | A61M 13/003 600/101 |
| 7,479,106 B2 * | 1/2009 | Banik | ................ | A61B 1/00068 600/118 |
| 7,569,027 B2 * | 8/2009 | Uesugi | ................ | A61M 13/003 604/23 |
| 7,704,223 B2 * | 4/2010 | Mantell | ............ | A61M 13/003 604/24 |
| 7,722,559 B2 * | 5/2010 | Uesugi | ................ | A61M 13/003 600/560 |
| 7,854,724 B2 * | 12/2010 | Stearns | ............. | A61B 17/3421 604/164.01 |
| 7,981,072 B2 * | 7/2011 | Uesugi | ................ | A61M 13/003 600/560 |
| 7,988,656 B2 * | 8/2011 | Uesugi | ............... | A61B 1/00135 128/898 |
| 8,007,282 B2 * | 8/2011 | Gregorio | ............... | G09B 23/285 434/262 |
| 8,052,644 B2 * | 11/2011 | Radgowski | ......... | A61M 1/0058 604/118 |
| 8,105,267 B2 * | 1/2012 | Mantell | ............ | A61M 13/003 604/26 |
| 8,221,310 B2 * | 7/2012 | Saadat | ................ | A61B 1/0008 600/104 |
| 8,231,523 B2 * | 7/2012 | Uesugi | ............... | A61B 1/00068 600/118 |
| 8,322,365 B2 * | 12/2012 | Wilson | ................ | A61M 27/006 137/530 |
| 8,323,181 B2 * | 12/2012 | Mukherjee | ............. | A61B 1/042 600/108 |
| 8,361,041 B2 * | 1/2013 | Fang | ..................... | A61B 1/042 600/109 |
| 8,416,291 B2 * | 4/2013 | Carrey | ............... | A61B 1/00039 348/77 |
| 8,591,459 B2 * | 11/2013 | Clymer | ............ | A61B 10/0283 600/562 |
| 8,734,381 B2 * | 5/2014 | Noda | ............... | A61M 13/003 604/23 |
| 8,840,580 B2 * | 9/2014 | Uesugi | ................ | A61B 50/13 600/560 |
| 2003/0078476 A1 * | 4/2003 | Hill | .................... | A61B 1/00052 600/160 |

(56) References Cited

U.S. PATENT DOCUMENTS

| | | | |
|---|---|---|---|
| 2003/0226566 A1* | 12/2003 | Dhuper | A61M 16/04 128/207.15 |
| 2004/0253183 A1* | 12/2004 | Uber, III | A61K 49/223 424/9.52 |
| 2005/0085690 A1* | 4/2005 | Tien | A61B 1/00105 600/109 |
| 2005/0137529 A1* | 6/2005 | Mantell | A61M 13/003 604/129 |
| 2005/0217727 A1* | 10/2005 | Uesugi | A61M 13/003 137/315.01 |
| 2005/0222491 A1* | 10/2005 | Noda | A61M 13/003 600/104 |
| 2005/0222534 A1* | 10/2005 | Uesugi | A61B 50/13 604/26 |
| 2005/0222535 A1* | 10/2005 | Uesugi | A61B 1/00039 604/26 |
| 2005/0234391 A1* | 10/2005 | Uesugi | A61M 13/003 604/24 |
| 2006/0004322 A1* | 1/2006 | Uesugi | A61M 13/003 604/26 |
| 2006/0030751 A1* | 2/2006 | Uesugi | A61B 1/00068 600/101 |
| 2006/0058617 A1* | 3/2006 | Sano | A61B 1/0005 600/407 |
| 2006/0079874 A1* | 4/2006 | Faller | A61B 17/32009 606/40 |
| 2006/0129087 A1* | 6/2006 | Uesugi | A61M 13/003 604/26 |
| 2007/0088275 A1* | 4/2007 | Stearns | A61B 17/3421 604/164.01 |
| 2007/0149926 A1* | 6/2007 | Moberg | A61M 5/1456 604/152 |
| 2007/0163585 A1* | 7/2007 | Uesugi | A61M 13/003 128/204.18 |
| 2007/0173760 A1* | 7/2007 | Fedenia | A61M 1/0023 604/131 |
| 2007/0233003 A1* | 10/2007 | Radgowski | A61M 1/0058 604/151 |
| 2007/0244363 A1* | 10/2007 | Sano | A61B 1/00039 600/158 |
| 2007/0255165 A1* | 11/2007 | Uesugi | A61B 1/00135 600/560 |
| 2007/0276183 A1* | 11/2007 | Melder | A61B 1/00011 600/112 |
| 2007/0293724 A1* | 12/2007 | Saadat | A61B 1/0008 600/156 |
| 2008/0200758 A1* | 8/2008 | Orbay | A61B 1/00048 600/112 |
| 2008/0287908 A1* | 11/2008 | Muni | A61B 17/24 604/506 |
| 2009/0259104 A1* | 10/2009 | Sato | A61B 1/00135 600/114 |
| 2009/0259172 A1* | 10/2009 | Yamaoka | A61B 1/00078 604/26 |
| 2010/0004506 A1* | 1/2010 | Saadat | A61B 1/0008 600/109 |
| 2010/0063437 A1* | 3/2010 | Nelson | A61B 17/3439 604/35 |
| 2010/0106080 A1* | 4/2010 | Uesugi | A61M 13/003 604/26 |
| 2010/0137802 A1* | 6/2010 | Yodfat | A61M 5/14248 604/152 |
| 2010/0241061 A1* | 9/2010 | Ott | A61B 17/3474 604/26 |
| 2010/0241185 A1* | 9/2010 | Mahapatra | A61N 1/0587 607/17 |
| 2010/0256558 A1* | 10/2010 | Olson | A61M 25/0147 604/95.01 |
| 2010/0268153 A1* | 10/2010 | Mantell | A61M 13/003 604/24 |
| 2011/0011398 A1* | 1/2011 | Yeates | A61M 15/0086 128/203.12 |
| 2011/0125084 A1* | 5/2011 | Stearns | A61B 17/3421 604/26 |
| 2011/0276058 A1* | 11/2011 | Choi | B25J 9/1671 606/130 |
| 2012/0116222 A1* | 5/2012 | Sawada | A61B 17/320068 600/439 |
| 2012/0165726 A1* | 6/2012 | Mantell | A61M 13/003 604/24 |
| 2012/0174022 A1* | 7/2012 | Sandhu | G06F 19/3406 715/781 |
| 2012/0184897 A1* | 7/2012 | Poll | A61B 1/015 604/24 |
| 2013/0123681 A1* | 5/2013 | Mantell | A61M 13/003 604/24 |
| 2013/0211320 A1* | 8/2013 | Alkhamesi | A61M 13/003 604/24 |
| 2013/0253368 A1* | 9/2013 | Are | A61B 1/00052 600/560 |
| 2013/0303852 A1* | 11/2013 | Hiraga | A61B 1/015 600/118 |
| 2014/0303550 A1* | 10/2014 | Williams | A61M 5/329 604/26 |
| 2014/0371667 A1* | 12/2014 | Kasuya | A61B 1/00135 604/26 |
| 2017/0173276 A1* | 6/2017 | Alkhamesi | A61M 11/02 |

FOREIGN PATENT DOCUMENTS

| | | |
|---|---|---|
| JP | 2006-288881 A | 10/2006 |
| JP | 2009-201555 A | 9/2009 |
| JP | 2012-231897 A | 11/2012 |
| WO | 2006/064713 A1 | 6/2006 |
| WO | 2007/080971 A1 | 7/2007 |

OTHER PUBLICATIONS

Jan. 6, 2015 Written Opinion issued in International Patent Application No. PCT/JP2014/076676.

Oct. 13, 2015 Office Action issued in Japanese Patent Application No. 2015-532640.

Feb. 23, 2016 Office Action issued in Japanese Patent Application No. 2015-532640.

Jan. 6, 2015 Search Report issued in International Patent Application No. PCT/JP2014/076676.

Jun. 28, 2017 Search Report issued in European Patent Application No. 14875694.3.

* cited by examiner

ABSTRACT

PNEUMOPERITONEUM APPARATUS

CROSS REFERENCE TO RELATED APPLICATION

This application is a continuation application of PCT/JP2014/076676 filed on Oct. 6, 2014 and claims benefit of Japanese Application No. 2013-269993 filed in Japan on Dec. 26, 2013, the entire contents of which are incorporated herein by this reference.

BACKGROUND OF INVENTION

1. Field of the Invention

The present invention relates to a pneumoperitoneum apparatus for performing pneumoperitoneum through an endoscope conduit inside an endoscope.

2. Description of the Related Art

In recent years, endoscopes have widely been used in a medical field. A flexible endoscope, which is an endoscope including a flexible insertion portion, is inserted along an inside of a curved body cavity (or a lumen) and pneumoperitoneum operation (or insufflation operation) for inflating the body cavity (or the lumen) with gas using a pneumoperitoneum apparatus (also referred to as an insufflation apparatus) is performed at a region to be examined or treated, whereby a field view of observation via the flexible endoscope and/or a space for performing treatment are secured. Also, there are various types of flexible endoscopes including respective insertion portions having, e.g., different internal diameters depending on organs or regions to be examined, and there are various types of insufflation conduits for insufflation ranging from thin ones to thick ones depending on the types of flexible endoscopes.

For example, in the conventional example in International Publication No. WO 2007/080971, it is disclosed that: the distal end side of an insertion portion of an endoscope is inserted into an abdominal cavity, pneumoperitoneum is performed inside an abdominal cavity using a pneumoperitoneum apparatus; and concurrently, a flow rate sensor measures a flow rate and outputs the flow rate to a controller and the controller adjusts the flow rate via an electro-pneumatic proportional valve. In this conventional example, although a flexible endoscope is used, the pneumoperitoneum apparatus performs pneumoperitoneum inside the abdominal cavity without using an insufflation conduit that is an endoscope conduit inside the flexible endoscope.

SUMMARY OF THE INVENTION

A pneumoperitoneum apparatus according to an aspect of the present invention includes: an insufflation gas source for insufflation; an insufflation conduit for pneumoperitoneum, the insufflation conduit being connected to the insufflation gas source and feeding insufflation gas for pneumoperitoneum; an endoscope connection tube connecting the insufflation conduit for pneumoperitoneum and an endoscope insufflation conduit provided inside an endoscope including an insertion portion; an insufflation flow rate measuring section provided on the insufflation conduit for the pneumoperitoneum, the insufflation flow rate measuring section being configured so as to measure an insufflation flow rate as a measured flow rate; a flow rate setting section configured so as to set the insufflation flow rate measured by the insufflation flow rate measuring section to a set flow rate that is larger than 0; an insufflation flow rate adjusting section provided on the insufflation conduit for pneumoperitoneum, the insufflation flow rate adjusting section being configured so as to, if the measured flow rate measured by the insufflation flow rate measuring section is not equal to the set flow rate, change an adjustment value for the insufflation flow rate to adjust the insufflation flow rate of insufflation to the endoscope insufflation conduit; an adjustment value storing section configured so as to, if the measured flow rate measured by the insufflation flow rate measuring section is equal to the set flow rate, store the adjustment value for the insufflation flow rate adjusting section; and a control section configured so as to, if the measured flow rate measured by the insufflation flow rate measuring section varies to a value that is equal to or below a threshold value after the measured flow rate reaches the set flow rate, perform control to set the adjustment value read from the adjustment value storing section for the insufflation flow rate adjusting section.

DETAILED DESCRIPTION OF THE PREFERRED EMBODIMENT(S)

Embodiments of the present invention will be described below with reference to the drawings.

First Embodiment

Figure 1:
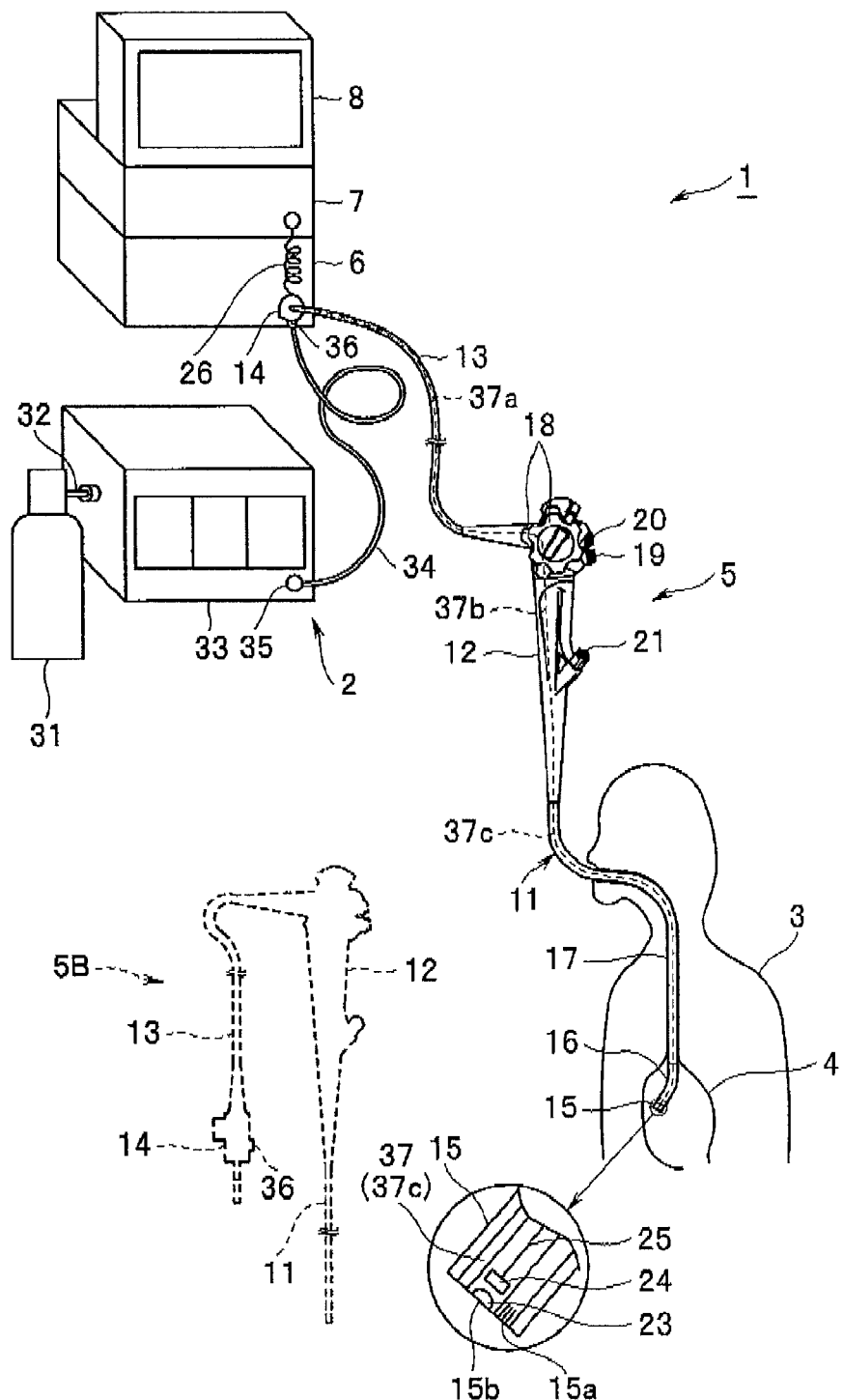
FIG. 1 is a diagram illustrating an overall configuration of an endoscope system including a pneumoperitoneum apparatus according to a first embodiment of the present invention.

As illustrated in FIG. 1, an endoscope system 1 includes: a pneumoperitoneum apparatus 2 according to a first embodiment of the present invention; a flexible endoscope 5, which is an endoscope including a flexible insertion portion to be inserted to an organ (digestive organ 4 in FIG. 1) inside a body cavity of a patient 3; a light source apparatus 6 that supplies illuminating light to the flexible endoscope 5; a video processor 7, which is a signal processing apparatus that performs signal processing of a signal from an image pickup device 24 provided in the flexible endoscope 5; and a monitor 8 that, upon input of a video signal generated by the video processor 7, displays an image picked up by the image pickup device 24 as endoscopic image.

The flexible endoscope 5 includes a flexible insertion portion 11, which can be inserted into a curved body cavity, an operation portion 12 to be grasped by a user such as a surgeon to perform various operations, the operation portion 12 being provided at a rear end of the insertion portion 11, and a flexible universal cable 13 extending out from the operation portion 12, and a connector 14 at an end portion of the universal cable 13 is detachably connected to the light source apparatus 6.

The insertion portion 11 includes a distal end portion 15 provided at a distal end, a bendable bending portion 16 provided at a rear end of the distal end portion 15, and a flexible tube portion 17 extending from a rear end of the bending portion 16 to a front end of the operation portion 12.

At the operation portion 12, a bending operation knob 18 to be operated to bend the bending portion 16 in a desired bending direction is provided, and an insufflation button 19 to be operated for insufflation and a suction button 20 to be operated for suction are provided. Also, in the vicinity of the front end of the operation portion 12, a treatment instrument insertion port 21 from which a treatment instrument is to be inserted is provided. The insufflation button 19 has an insufflation switching button function that performs first switching of a later-described endoscope insufflation conduit 37 provided in the flexible endoscope 5 from a closed state to an open state and second switching of the endoscope insufflation conduit 37 from an open state to a closed state.

The light source apparatus 6 supplies illuminating light generated inside the light source apparatus 6 to a light guide connector provided in the connector 14 of the flexible endoscope 5.

The illuminating light supplied to the light guide connector emitted from an illumination window 15a at the distal end portion 15 of the insertion portion 11 through a light guide 22 inserted inside, e.g., the universal cable 13 of the flexible endoscope 5 and illuminates an object such as a diseased part (see an enlarged view in the vicinity of the distal end portion 15 in FIG. 1).

At the distal end portion 15, an observation window 15b is provided adjacent to the illumination window 15a, and in the observation window 15b, an objective lens 23 that forms an optical image of the illuminated object is disposed, and at a position at which the image from the objective lens 23 is formed, an image pickup device 24 is disposed. The image pickup device 24 is connected to the video processor 7 via a signal wire 25 inserted inside the flexible endoscope 5 and a connection cable 26 connected to the connector 14.

The pneumoperitoneum apparatus 2 includes a carbon dioxide gas bottle 31 providing an insufflation gas source for insufflation, a pneumoperitoneum apparatus body 33 to which the carbon dioxide gas bottle 31 is connected via a connection conduit 32, and an endoscope connection tube 34 that feeds insufflation gas adjusted by the pneumoperitoneum apparatus body 33 to the flexible endoscope 5.

The insufflation gas adjusted by the pneumoperitoneum apparatus body 33 is fed to the endoscope insufflation conduit 37 (inside the flexible endoscope 5) (see the enlarged view), which is connected to an insufflation pipe sleeve 36 in the connector 14 of the flexible endoscope 5 and thereby communicates with the insufflation pipe sleeve 36 via the endoscope connection tube 34 connected to an insufflation pipe sleeve 35.

Figure 2:
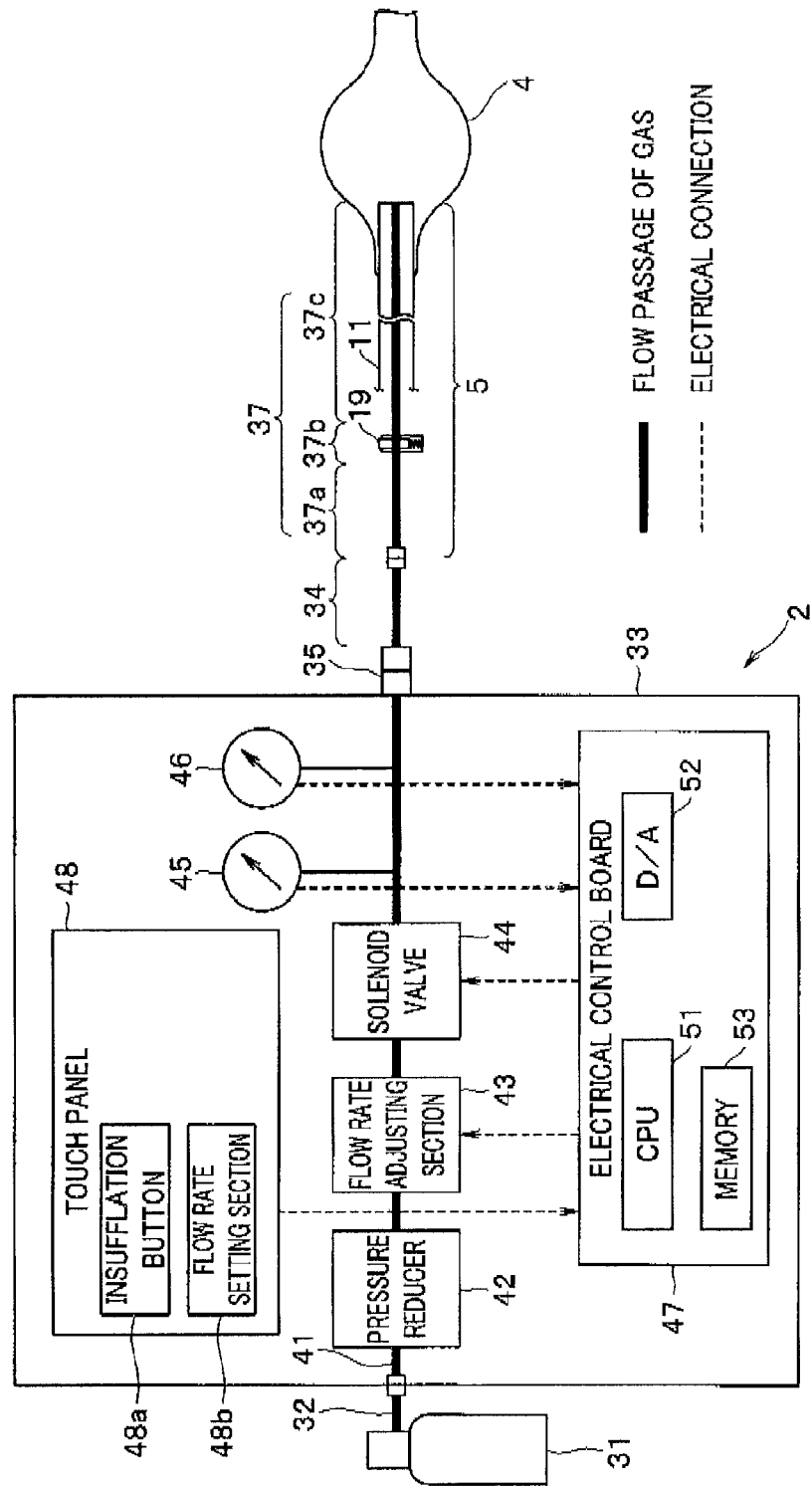
FIG. 2 is a diagram illustrating a configuration of the pneumoperitoneum apparatus according to the first embodiment.

Note that as illustrated in FIG. 2, the endoscope insufflation conduit 37 includes an endoscope insufflation conduit 37a inside the universal cable 13, an endoscope insufflation conduit 37b in the vicinity of the insufflation button 19 inside the operation portion 12, and an endoscope insufflation conduit 37c inside the insertion portion 11.

The insufflation gas fed to the endoscope insufflation conduit 37 is fed from a distal end opening in the distal end portion 15 of the insertion portion 11 to the inside of the digestive organ 4 outside the distal end portion 15, to which the distal end portion 15 of the insertion portion 11 is inserted, and provides pneumoperitoneum so as to inflate the digestive organ 4 with the insufflation gas. The inflation of the digestive organ 4 facilitates observation of the inside of the digestive organ 4.

Note that although one flexible endoscope 5 is illustrated in FIG. 1, for example, as indicated by the dotted line, a flexible endoscope 5B including, for example, a smaller-diameter insertion portion 11 may be used.

The flexible endoscope 5B includes an endoscope insufflation conduit having a diameter that is smaller than that of the endoscope insufflation conduit 37 in the flexible endoscope 5. A configuration of the flexible endoscope 5B is substantially similar to that of the flexible endoscope 5. Also, a flexible endoscope including an endoscope insufflation conduit having a diameter that is larger than that of the endoscope insufflation conduit 37 in the flexible endoscope 5 may be used in endoscopy (not illustrated).

FIG. 2 illustrates a configuration of the pneumoperitoneum apparatus 2 and the inside of the pneumoperitoneum apparatus body 33.

As illustrated in FIG. 2, the connection conduit 32 connected to the carbon dioxide gas bottle 31, which provides an insufflation gas source, is connected to one end portion of an insufflation conduit 41 for pneumoperitoneum inside a casing of the pneumoperitoneum apparatus body 33, and the other end portion of the insufflation conduit 41 extends to the insufflation pipe sleeve 35. Note that the one end portion of the insufflation conduit 41 for pneumoperitoneum may be made to project outside the casing of the pneumoperitoneum apparatus body 33 to provide a structure connecting the carbon dioxide gas bottle 31 without using the connection conduit 32.

On the insufflation conduit 41 for pneumoperitoneum, as described below, a pressure reducer 42, a flow rate adjusting section (or a flow rate adjuster) 43, a solenoid valve 44, a pressure sensor 45 and a flow rate sensor 46 are disposed. Also, as indicated by dotted lines, the flow rate adjusting section 43, the solenoid valve 44, the pressure sensor 45 and the flow rate sensor 46 are connected to an electrical control board 47 via signal wires.

Also, in a touch panel 48 provided in the pneumoperitoneum apparatus body 33, an insufflation button 48a for performing operation to provide an instruction to start and stop insufflation, and a flow rate setting section (or a flow rate setter) 48b including, e.g., a flow rate setting knob for setting a set flow rate as an insufflation flow rate suitable for pneumoperitoneum are provided. A signal generated in response to an instruction provided by operation of the insufflation button 48a by a user is sent to the electrical control board 47 via a signal wire, and the electrical control board 47 performs control operation according to the instruction. Also, the electrical control board 47 performs control operation to adjust an insufflation flow rate via the flow rate adjusting section 43 so that a measured flow rate measured by the flow rate sensor 46 becomes a target set flow rate set by the flow rate setting section 48b.

Figure 3:
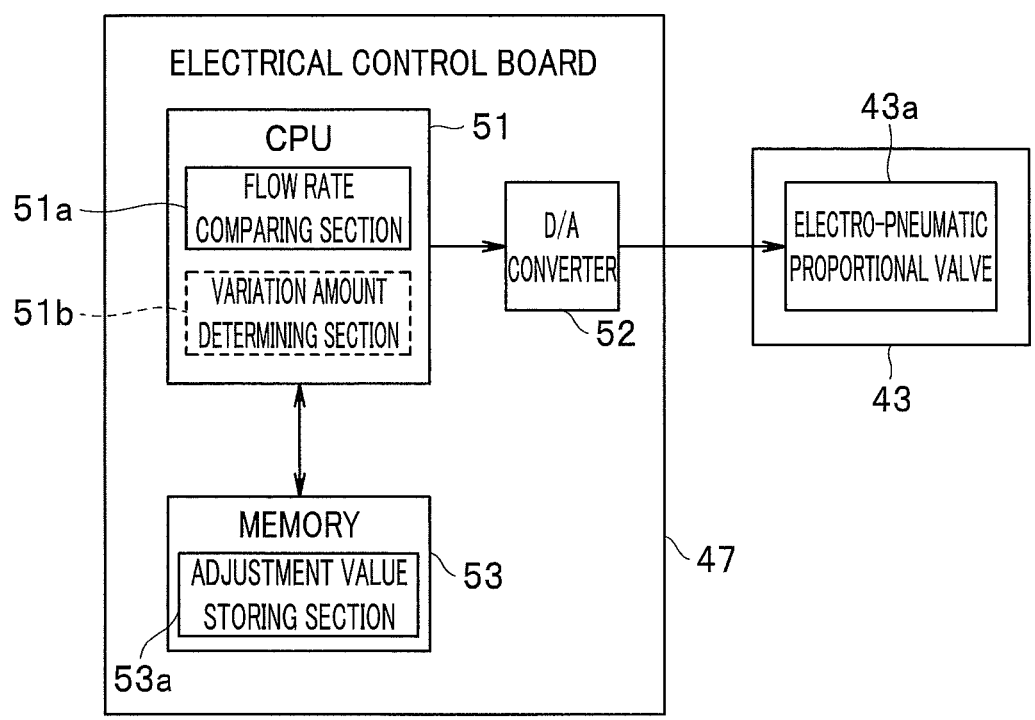
FIG. 3 is a flowchart illustrating a procedure of insufflation operation performed by the pneumoperitoneum apparatus according to the first embodiment.

The pressure reducer 42 reduces a pressure of carbon dioxide gas, which is insufflation gas fed from the carbon dioxide gas bottle 31, and sends the carbon dioxide gas to the flow rate adjusting section 43. The flow rate adjusting section 43 adjusts a flow rate of the insufflation gas fed from the insufflation conduit 41 for pneumoperitoneum (insufflation flow rate). As illustrated in FIG. 3, the flow rate adjusting section 43 includes an electro-pneumatic proportional valve 43a that controls, for example, the pressure of the insufflation gas inputted in proportion to a voltage level of a control signal in a stepless manner and thereby adjusts the insufflation flow rate of the insufflation gas.

The insufflation gas adjusted by the flow rate adjusting section 43 is fed to the insufflation pipe sleeve 35 side through the solenoid valve 44, opening and closing of which are controlled by a valve opening/closing signal from the electrical control board 47. Also, on a part of the insufflation conduit 41 for pneumoperitoneum between the solenoid valve 44 and the insufflation pipe sleeve 35, the pressure sensor 45 that measures the pressure of the insufflation gas and the flow rate sensor 46 that measures the insufflation flow rate are disposed, and each of the measured insufflation pressure (also referred to "measured pressure") and the measured insufflation flow rate (also referred to "measured flow rate") is sent to the electrical control board 47.

The electrical control board 47 includes, for example, as illustrated in FIG. 3, a central processing unit (abbreviated as "CPU") 51, a D/A converter 52 that converts a digital voltage value for controlling the insufflation pressure in the electro-pneumatic proportional valve 43a, which is included in the flow rate adjusting section 43, from the CPU 51 into an analog voltage value and outputs the analog voltage value, and a memory 53, which is a storage section (or a storage device) that stores a control program for the CPU 51 and stores a value corresponding to an insufflation pressure value for the electro-pneumatic proportional valve 43a when the measured flow rate is equal to the set flow rate, as an adjustment value.

Note that the endoscope insufflation conduit 37 in the flexible endoscope 5 is brought into an open state as a result of depression of the insufflation button 19 in the operation portion 12, and is brought into a closed state as a result of the insufflation button 19 being not depressed or a finger depressing the insufflation button 19 being moved away from the insufflation button 19. FIG. 2 illustrates an open state in which the insufflation button 19 is depressed by a finger. More specifically, as illustrated in FIG. 4A, inside a cylinder 55 including openings 55a and 55b provided at respective positions at which the openings 55a and 55b face respective parts of the endoscope insufflation conduit 37 on the opposite sides of the insufflation button 19 so as to communicate with the respective parts, the insufflation button 19 having a columnar shape is disposed so as to be slidable in a longitudinal direction thereof, and the insufflation button 19 is biased in a direction in which the insufflation button 19 projects from an opening at an upper end of the cylinder 55, by a spring 56 disposed on the bottom portion side of the cylinder 55, a diameter of the bottom portion side being reduced in a stepped manner.

Figure 4A:
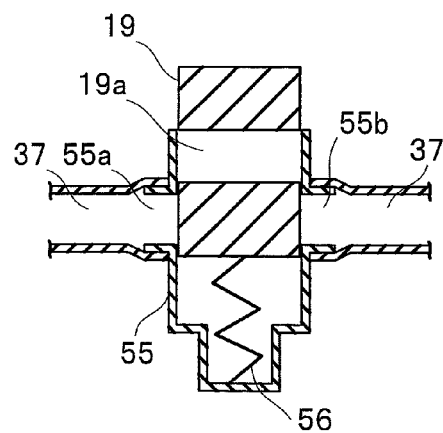
FIG. 4A is a cross-sectional view illustrating a schematic configuration of a flexible endoscope with an insufflation button closed.

Also, in the insufflation button 19, a traverse hole 19a is provided in the vicinity of a center position in the longitudinal direction thereof; however, as illustrated in FIG. 4A, the openings 55a and 55b and the traverse hole 19a are kept in a state in which the openings 55a and 55b and the traverse hole 19a do not communicate with each other, that is, are each kept in an occluded state.

Figure 4B:
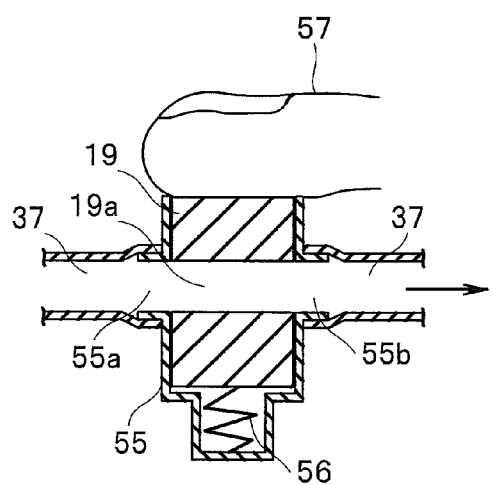
FIG. 4B is a cross-sectional view illustrating the schematic configuration in FIG. 4A in an open state.

In the state in FIG. 4A, upon the insufflation button 19 being depressed by a finger 57 to a position at which the insufflation button 19 abuts the stepped portion, as illustrated in FIG. 4B, the openings 55a and 55b and the traverse hole 19a are brought into communication with each other. As a result of the insufflation button 19 being operated in such a manner as described above, the endoscope insufflation conduit 37 can be set to an occluded state and an open state.

Thus, even if the insufflation button 48a provided in the pneumoperitoneum apparatus body 33 is turned on, no insufflation can actually be performed for a region to be subjected to pneumoperitoneum (digestive organ 4) unless the insufflation button 19 in the flexible endoscope 5 is turned on.

When the insufflation button 48a provided in the pneumoperitoneum apparatus body 33 is on, if the insufflation button 19 in the flexible endoscope 5 is turned on, insufflation operation is actually started, and the measured flow rate increases from 0.

In the present embodiment, when the measured flow rate varies from 0, the CPU 51 compares the measured flow rate with a set flow rate set in advance. Thus, as illustrated in FIG. 3, the CPU 51 has a function of a flow rate comparing section (or a flow rate comparing circuit) 51a that compares the measured flow rate measured by the flow rate sensor 46 and the set flow rate.

The flow rate comparing section 51a includes a comparison circuit. Note that a variation amount determining section 51b, which is indicated by the dotted line in FIG. 3, is used in a later-described second embodiment.

The CPU 51 performs control so that the insufflation pressure value, which is an adjustment value for adjusting the flow rate via the electro-pneumatic proportional valve 43a included in the flow rate adjusting section 43, is adjusted in a stepwise manner according to a result of the comparison by the flow rate comparing section 51a and the flow rate has a value equal to the set flow rate. In other words, (the electro-pneumatic proportional valve 43a in) the flow rate adjusting section 43 controlled by the CPU 51 provides an insufflation flow rate adjusting section (or an insufflation flow rate adjuster) that if the measured flow rate is not equal to the set flow rate, changes the adjustment value to adjust the insufflation flow rate of the insufflation (to the endoscope insufflation conduit 37).

In this case, where a result of comparison between the measured flow rate from the flow rate sensor 46 and the set flow rate indicates that the measured flow rate and the set flow rate are not equal to each other, the CPU 51 performs control so that if the measured flow rate is smaller than the set flow rate, the insufflation pressure value in the electro-pneumatic proportional valve 43*a* is increased so as to increase the measured flow rate, and conversely, if the measured flow rate is larger than the set flow rate, the insufflation pressure value in the electro-pneumatic proportional valve 43*a* is decreased so as to decrease the measured flow rate.

Note that the CPU 51 performs control so that if the measured flow rate measured by the flow rate sensor 46 becomes a measured flow rate of 0 after the measured flow rate reaches the set flow rate, the flow rate adjustment operation in the flow rate adjusting section 43 is stopped, and if the measured flow rate is not 0 (the measured flow rate is larger than 0), the flow rate adjusting section 43 performs flow rate adjustment operation. Regarding the state in which the measured flow rate is 0, the CPU 51 compares the measured flow rate with a threshold value that is slightly larger than 0, and if the measured flow rate is equal to or below the threshold value, detects that the measured flow rate is 0.

Also, in the present embodiment, if the result of comparison by the flow rate comparing section 51*a* indicates that the measured flow rate from the flow rate sensor 46 is equal to the set flow rate, the CPU 51 stores the adjustment value (for the electro-pneumatic proportional valve 43*a*) from the flow rate adjusting section 43 in the memory 53. Thus, the memory 53 has a function of an adjustment value storing section (adjustment value storing device) 53*a* or an insufflation pressure value storing section (insufflation pressure value storing device) that if a result of comparison indicates that a measured flow rate is equal to a set flow rate, stores an adjustment value for the flow rate adjusting section 43.

Also, in the present embodiment, if the measured flow rate from the flow rate sensor 46 is equal to 0, the CPU 51 performs control to set the adjustment value read from the adjustment value storing section 53*a* included in the memory 53, as an adjustment value to be used on or after a current time in the electro-pneumatic proportional valve 43*a* in the flow rate adjusting section 43 providing the insufflation flow rate adjusting section. In other words, if the measured flow rate from the flow rate sensor 46 is equal to 0, the CPU 51 has a function of a control section (or a control circuit) that performs control to set (update) the adjustment value set for the flow rate adjusting section 43, to an adjustment value that is an insufflation pressure value read from the adjustment value storing section 53*a*.

A supplemental description of the function of the CPU 51 as the control section will be provided. As can be understood from the above-described configuration, since no electric signal is generated, when the insufflation button 19 in the flexible endoscope 5 is turned on or off, the electrical control board 47 providing control means for the pneumoperitoneum apparatus body 33 side continues the operation of the flow rate adjusting section 43, which provides the insufflation flow rate adjusting section, adjusting the insufflation flow rate immediately after the insufflation button 19 is turned off from on, and when the measured flow rate varies from the set flow rate (in this case, since the endoscope insufflation conduit 37 is brought into a closed state, the measured flow rate decrease toward 0), changes the adjustment value from the adjustment value corresponding to the set flow rate.

As a result of such variation as above, next time the insufflation button 19 is turned on from off, operation of adjusting an insufflation flow rate is performed (started) using the adjustment value varied from the desirable adjustment value.

In the present embodiment, as described above, if the measured flow rate from the flow rate sensor 46 is equal to 0 (in other words, if the measured flow rate varies to a value that is equal to or below the threshold value that is slightly larger than 0), it is detected based on the measured flow rate that the endoscope insufflation conduit 37 is set to a closed state (or switched from an open state to a closed state) as a result of the insufflation button 19 in the flexible endoscope 5 being turned off from on. Then, upon the detection of the endoscope insufflation conduit 37 being set to a closed state as described above, an adjustment value read from the adjustment value storing section 53*a* (which stores an adjustment value when the measured flow rate is equal to the set flow rate) is set for the electro-pneumatic proportional valve 43*a* in the flow rate adjusting section 43. As a result of the setting as above, next time the insufflation button 19 is turned on from off, operation of adjusting the insufflation flow rate for the flow rate adjusting section 43 can be started using the adjustment value corresponding to the set flow rate as an initial value (initial set value).

The pneumoperitoneum apparatus 2 according to the present embodiment includes: the carbon dioxide gas bottle 31 as an insufflation gas source for insufflation; the insufflation conduit 41 for pneumoperitoneum, the insufflation conduit 41 being connected to the insufflation gas source (using the connection conduit 32 or without using the connection conduit 32) and feeding insufflation gas for pneumoperitoneum; the endoscope connection tube 34 connecting the insufflation conduit 41 for pneumoperitoneum and the endoscope insufflation conduit 37 provided inside the flexible endoscope 5, which is an endoscope including a flexible insertion portion 11; the flow rate sensor 46 as an insufflation flow rate measuring section provided on the insufflation conduit 41 for pneumoperitoneum, the insufflation flow rate measuring section being configured so as to measure the insufflation flow rate as a measured flow rate; the flow rate setting section 48*b*, which provides a set flow rate setting section configured so as to, in order to make the insufflation flow rate measured by the insufflation flow rate measuring section reach a target set flow rate, set the set flow rate in advance; the flow rate adjusting section 43, which provides an insufflation flow rate adjusting section provided on the insufflation conduit 41 for pneumoperitoneum, the insufflation flow rate adjusting section being configured so as to, if the measured flow rate measured by the insufflation flow rate measuring section is not equal to the set flow rate, change an adjustment value for the insufflation flow rate to adjust the insufflation flow rate for the endoscope insufflation conduit 37; the memory 53 as a storage device including the adjustment value storing section 53*a* configured to, if the measured flow rate measured by the insufflation flow rate measuring section is equal to the set flow rate, store the adjustment value for the insufflation flow rate adjusting section; and the CPU 51, which functions as a control section configured so as to, if the measured flow rate measured by the insufflation flow rate measuring section varies to a value that is equal to or below a threshold value after the measured flow rate reaches the set flow rate (if the measured flow rate varies to a value that is equal to 0 in the present embodiment), perform control to set the adjustment value read from the adjustment value storing section for the insufflation flow rate adjusting section.

Figure 5:
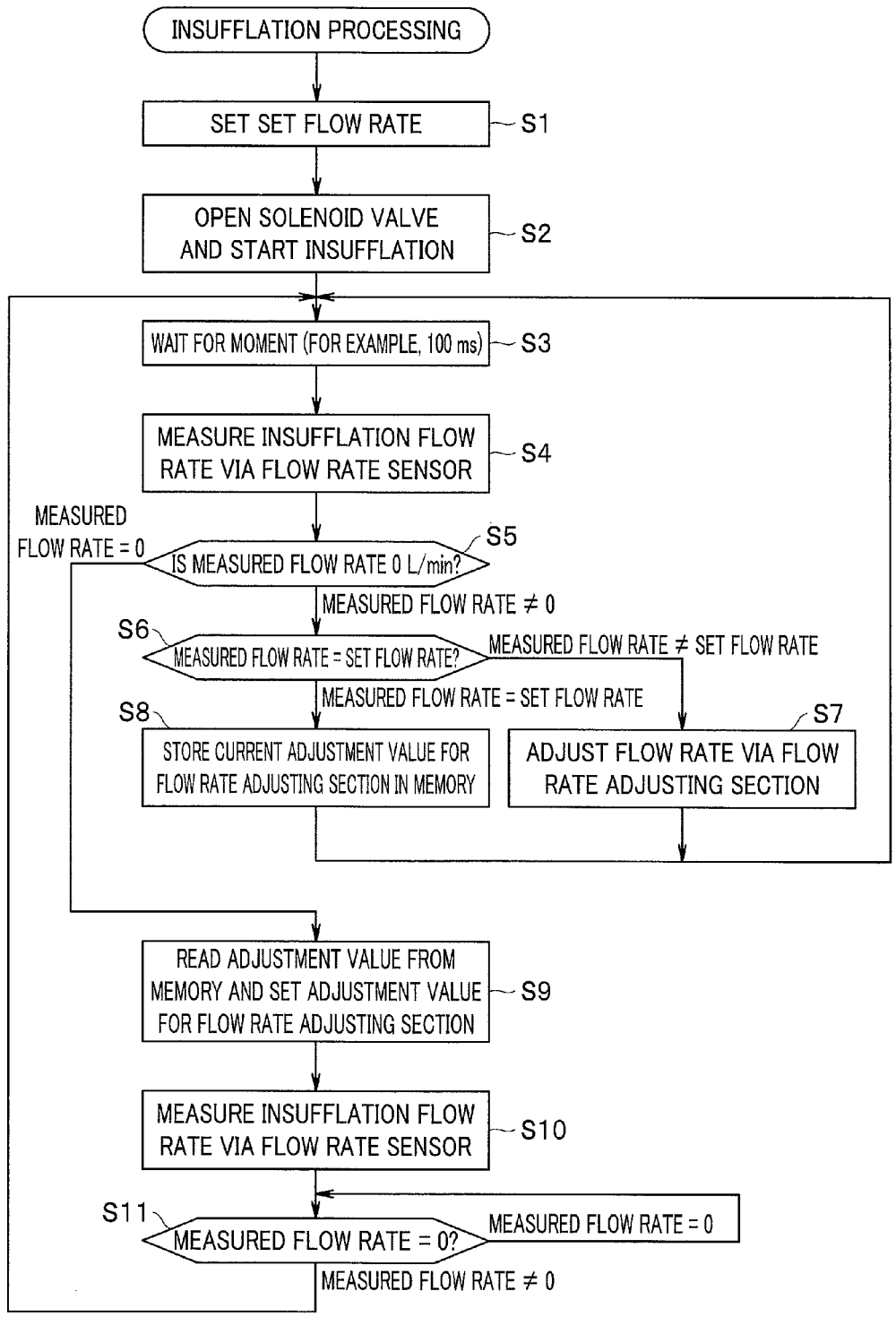
FIG. 5 is a flowchart illustrating a procedure for insufflation processing in the pneumoperitoneum apparatus according to the first embodiment.
Figure 7:
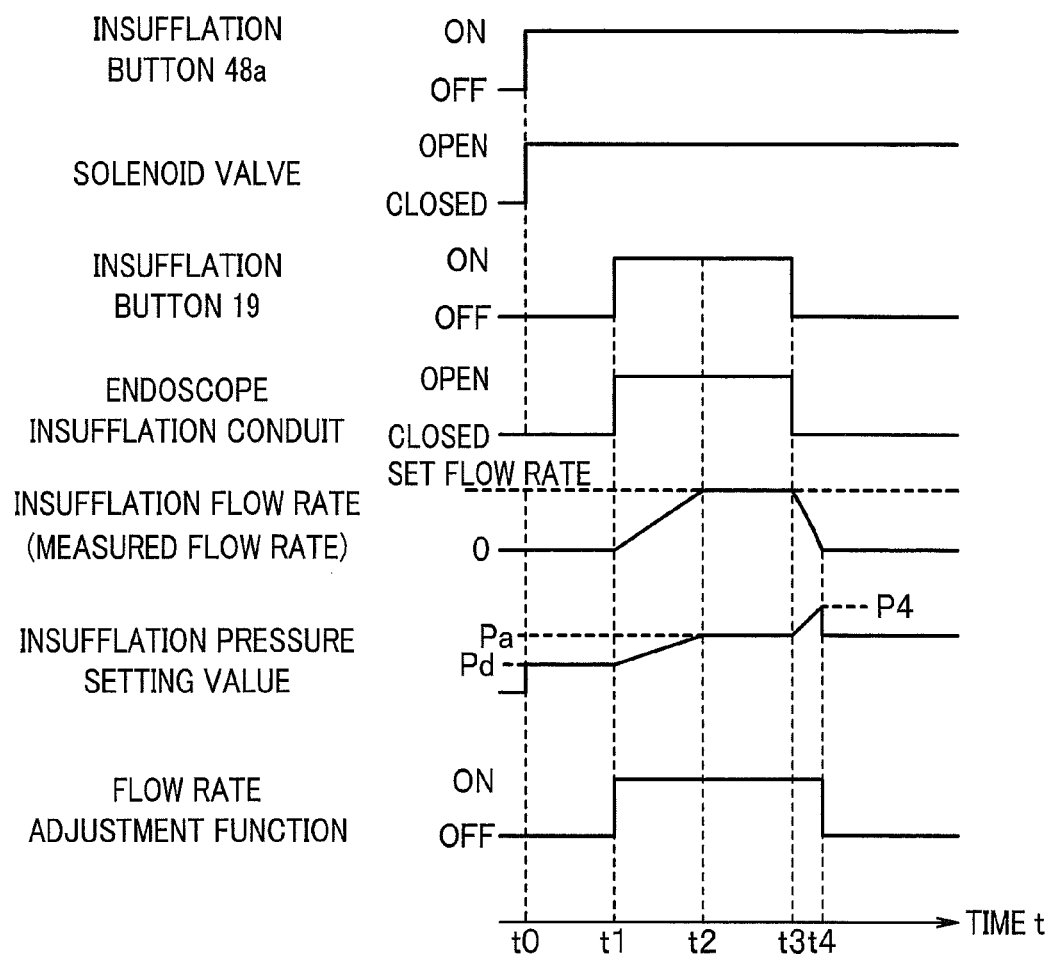
FIG. 7 is a timing chart indicating operation of the pneumoperitoneum apparatus according to the first embodiment.

Next, operation of the present embodiment will be described. FIG. 5 is a flowchart of overall operation of the pneumoperitoneum apparatus 2, and FIG. 7 is a timing chart.

As illustrated in FIG. 5, upon start of insufflation processing, in first step S1, a user operates the flow rate setting section 48b in the touch panel 48 to set a target set flow rate such as a desired insufflation flow rate in pneumoperitoneum. Subsequently, the insufflation button 48a in the touch panel 48 is turned on and as indicated in step S2, the CPU 51 thereby opens the solenoid valve 44 to start insufflation operation. Here, if a set flow rate is previously set and such previous set flow rate is used, the processing in step S1 can be omitted.

Also, upon the user turning the insufflation button 19 of the flexible endoscope 5 on, the insufflation operation is actually started.

As indicated in step S3, the CPU 51 waits for a moment (for example, 100 ms) after the processing in step S2.

After a lapse of a moment, as indicated in step S4, the flow rate sensor 46 measures an insufflation flow rate. In other words, the CPU 51 acquires an insufflation flow rate measured by the flow rate sensor 46 after a lapse of a moment from step S3 as a measured flow rate.

Next, in step S5, the CPU 51 determines whether or not the measured flow rate is 0 L/min, which is an insufflation flow rate of 0. When the insufflation button 19 in the flexible endoscope 5 is on, the measured flow rate has a positive value that is not 0.

If a result of the determination indicates that the measured flow rate is not 0, in next step S6, the CPU 51 determines whether or not the measured flow rate is equal to the set flow rate set in step S1. When only a short period of time has passed from the actual start of the insufflation operation as a result of the insufflation buttons 48a and 19 being turned on, the measured flow rate has not yet reached the set flow rate. In this case, the CPU 51 determines that the measured flow rate is not equal to the set flow rate.

If a result of the determination indicates that the measured flow rate is not equal to the set flow rate, in next step S7, the CPU 51 performs control so that the flow rate adjusting section 43 performs flow rate adjustment. The processing in step S7 will be described later with reference to FIG. 6.

After the processing in step S7, the operation returns to the processing in step S3. Repetition of the processing in steps S3 to S7 causes the measured flow rate to be equal to the set flow rate. When the measured flow rate becomes equal to the set flow rate, in step S6, the CPU 51 determines that the measured flow rate is equal to the set flow rate, and proceeds to processing in step S8.

In step S8, the CPU 51 performs control to store a current adjustment value for the flow rate adjusting section 43 (that is, an adjustment value for the flow rate adjusting section 43 when the measured flow rate is equal to the set flow rate) in the memory 53. Also, the CPU 51 controls the flow rate adjustment by the flow rate adjusting section 43 to keep the adjustment value when the measured flow rate is equal to the set flow rate. In this state, the adjustment value for the flow rate adjusting section 43 is a fixed insufflation pressure setting value corresponding to the set flow rate (see the insufflation pressure setting value in FIG. 7).

After the processing in step S8, the operation returns to the processing in step S3. In a state in which the measured flow rate is equal to the set flow rate, when sufficient pneumoperitoneum is provided inside the digestive organ 4 using carbon dioxide gas as insufflation gas, the user turns the insufflation button 19 off from on to stop the insufflation, and the endoscope insufflation conduit 37 is brought into a closed state from an open state.

In this case, after a lapse of a short period of time after the insufflation button 19 being turned off, the measured flow rate measured by the flow rate sensor 46 becomes 0. Then, in step S5, the CPU 51 determines that the measured flow rate is 0 (because the measured flow rate becomes equal to or below a threshold value that is close to 0). If a result of the determination indicates that the measured flow rate is equal to 0, in step S9, the CPU 51 reads the adjustment value stored in the memory 53 from the memory 53, and sets the read adjustment value for the flow rate adjusting section 43.

More specifically, where, for example, a digital adjustment value stored in the memory 53 is Va, an analog adjustment value Va obtained by conversion of the adjustment value Va by the D/A converter 52 is set for the electro-pneumatic proportional valve 43a in the flow rate adjusting section 43. Also, the CPU 51 performs control to stop the flow rate adjustment by the electro-pneumatic proportional valve 43a. When (next time) the electro-pneumatic proportional valve 43a in the flow rate adjusting section 43 performs operation of adjusting an insufflation flow rate, the insufflation flow rate adjustment is to be started using the adjustment value Va as an initial value.

In next step S10 after (a lapse of a moment from) the processing in step S9, the flow rate sensor 46 measures the insufflation flow rate. Then, the CPU 51 acquires the measured insufflation flow rate (that is, the measured flow rate).

In next step S11, the CPU 51 determines whether or not the acquired measured flow rate is 0. If the measured flow rate is 0, the processing in step S11 is continued.

On the other hand, in some cases, the user turns the insufflation button 19 on again to resume gas insufflation after turning the insufflation button 19 off. In such cases, the measured flow rate becomes a value that is larger than 0, and thus, in step S11, the CPU 51 determines that the measured flow rate is not 0. In the case of this determination result, the CPU 51 activates the flow rate adjustment operation via the electro-pneumatic proportional valve 43a in the flow rate adjusting section 43 and returns to the processing in step S3 and repeats the above-described operation.

If the CPU 51 returns to step S3 and repeats the above-described operation, insufflation operation starts with the adjustment value stored in the memory 53 in step S9 before step S11 set for the electro-pneumatic proportional valve 43a in the flow rate adjusting section 43. In this case, the insufflation operation can be performed with the more desirable adjustment value.

Figure 6:
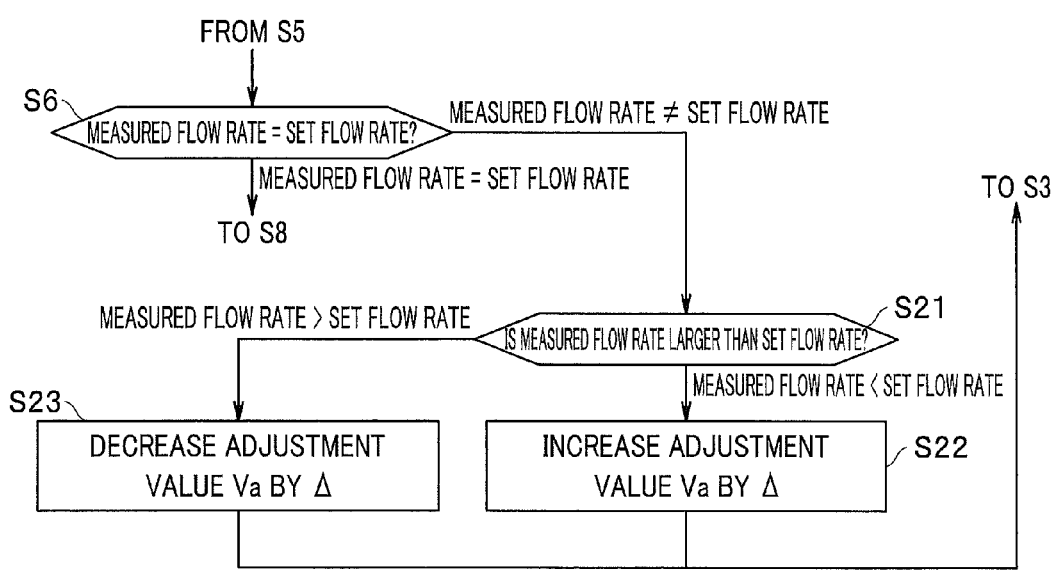
FIG. 6 is a flowchart illustrating processing for flow rate adjustment.

FIG. 6 indicates details of the processing in step S7. In the below description, it is assumed that the adjustment value for the electro-pneumatic proportional valve 43a in the flow rate adjusting section 43 when the processing in step S7 is started is Va. Note that the electro-pneumatic proportional valve 43a adjusts the insufflation flow rate according to the insufflation pressure setting value that varies in proportion to the adjustment value Va. Upon start of the processing for flow rate adjustment, in first step S21, the CPU 51 determines whether or not the measured flow rate measured by the flow rate sensor 46 is larger than the set flow rate.

If a result of the determination indicates that the measured flow rate is smaller than the set flow rate, in next step S22, the CPU 51 increases the adjustment value Va by a predetermined value Δ. In other words, the CPU 51 sets the adjustment value Va to Va+Δ and then proceeds to the processing in step S3. In this case, as a result of the increase in insufflation pressure, the insufflation flow rate increases.

Then, after the increase, in step S6, if the measured flow rate is not equal to the set flow rate, and in addition, in step S21, if the measured flow rate is smaller than the set flow rate, in next step S22, the CPU 51 further increases the adjustment value Va+Δ by the predetermined value Δ. The above-described control loop for insufflation flow rate adjustment enables the measured flow rate to be set to be equal to the set flow rate in a short period of time.

On the other hand, in step S21, if the result of the determination indicates that the measured flow rate is larger than the set flow rate, in step S23, the CPU 51 decreases the current adjustment value Va by the predetermined value Δ. In other words, the CPU 51 sets the adjustment value Va to Va−Δ and then proceeds to the processing in step S3.

In this case, as a result of the decrease in insufflation pressure setting value, the insufflation flow rate decreases. Then, after the decrease, in step S6, if the measured flow rate is not equal to the set flow rate, and in addition, in step S21, if the measured flow rate is larger than the set flow rate, in step S23, the CPU 51 further decreases the adjustment value Va−Δ by the predetermined value Δ.

The above-described control loop for insufflation flow rate adjustment enables the measured flow rate to be set to be equal to the set flow rate in a short period of time. Here, when the measured flow rate becomes equal to the set flow rate as described above, as indicated in step S8, the adjustment value set for the electro-pneumatic proportional valve 43a in the flow rate adjusting section 43 when the measured flow rate becomes equal to the set flow rate is stored in the memory 53.

FIG. 7 is a timing chart for the pneumoperitoneum apparatus 2, and the abscissa axis represents passage of time t. As illustrated in FIG. 7, upon the insufflation button 48a in the touch panel 48 in the pneumoperitoneum apparatus body 33 being turned on from off at, for example, a time t0, the CPU 51 opens the solenoid valve 44 and starts insufflation operation (on the pneumoperitoneum apparatus body 33 side). Also, for example, an insufflation pressure setting value Pd corresponding to an adjustment value at the time of initial operation (default insufflation pressure setting value in FIG. 7) is provided for the electro-pneumatic proportional valve 43a. Here, the insufflation pressure setting value indicated in FIG. 7 is different from a value in a part of the inside of the insufflation conduit 41 for pneumoperitoneum in the vicinity of the electro-pneumatic proportional valve 43a, which is measured by the pressure sensor 45.

Upon the user performing operation to turn the insufflation button 19 in the flexible endoscope 5 on from off at, for example, a time t1, the endoscope insufflation conduit 37 is brought into an open state from a closed state, and insufflation gas passed through the insufflation conduit 41 for pneumoperitoneum in the pneumoperitoneum apparatus body 33 with the insufflation pressure setting value Pd set for the electro-pneumatic proportional valve 43a is fed to the inside of the digestive organ 4 through the endoscope insufflation conduit 37.

Around a time immediately after the time t1 at which the insufflation button 19 is turned on, the measured flow rate measured by the flow rate sensor 46 increases from 0. If the measured flow rate does not reach the set flow rate, as described with reference to FIG. 6, the CPU 51 changes the adjustment value for the electro-pneumatic proportional valve 43a to adjust the insufflation flow rate.

Upon the increase of the measured flow rate from 0, the adjustment value greatly varies in a stepwise manner and the insufflation pressure also increases in a stepwise manner (in FIG. 7, in a linear manner because a value of each step is small).

As indicated in FIG. 7, during a period in which the measured flow rate has not yet reached the set flow rate (time t1 to t2), the insufflation pressure setting value increases. Then, at the time t2 at which the measured flow rate reaches the set flow rate, as indicated in step S8 in FIG. 5, the CPU 51 performs control to store the current adjustment value for the electro-pneumatic proportional valve 43a in the memory 53.

Also, the CPU 51 performs control to keep the current adjustment value for the electro-pneumatic proportional valve 43a when the measured flow rate is equal to the set flow rate. Therefore, the insufflation pressure setting value at and after the time t2 is a fixed insufflation pressure setting value Pa. The insufflation pressure setting value Pa corresponds to the adjustment value for the electro-pneumatic proportional valve 43a when the measured flow rate is equal to the set flow rate. Here, as indicated in FIG. 7, during a period in which the measured flow rate continues being equal to the set flow rate (t2 to t3), the CPU 51 performs control to store the current adjustment value for the electro-pneumatic proportional valve 43a in the memory 53, at short time intervals. In other words, the adjustment value stored in the memory 53 is overwritten by a temporally-new adjustment value and kept in the memory 53.

When the user turns the insufflation button 19 off from on at a time t3, which is a time at and after the time t2, the endoscope insufflation conduit 37 is brought into a closed state from the open state, the measured flow rate, which is the insufflation flow rate measured by the flow rate sensor 46, sharply decreases and becomes 0 at a time t4 after a short period of time immediately after the time t3. Immediately after the time t3, the flow rate adjustment function provided by the CPU 51 is operating ("ON" in FIG. 7).

Thus, when the measured flow rate of the flow rate sensor 46 becomes a value that is smaller than the set flow rate, the CPU 51 performs control to make an increase from the insufflation pressure setting value Pa, which is the adjustment value for the electro-pneumatic proportional valve 43a. Then, as indicated in FIG. 7, the insufflation pressure setting value increases from the time t3 to the time t4. The insufflation pressure setting value at the time t4 is indicated by P4.

Then, when the measured flow rate becomes close to 0 at the time t4, as described in step S9 in FIG. 5, the CPU 51 stops the flow rate adjustment operation via the electro-pneumatic proportional valve 43a, reads the adjustment value from the memory 53 and sets the adjustment value for the electro-pneumatic proportional valve 43a.

Here, this adjustment value is the adjustment value at the time t3 in FIG. 7 and the insufflation pressure setting value in this case corresponds to Pa. Therefore, upon the insufflation button 19 being turned on again at and after the time t4, the electro-pneumatic proportional valve 43a starts flow rate adjustment using the insufflation pressure setting value Pa as an initial value.

According to the present embodiment, which operates as described above, a measured flow rate is compared with a set flow rate and flow rate adjustment is performed so that the measured flow rate becomes equal to the set flow rate, and thus even if the flexible endoscope 5 whose endoscope insufflation conduit 37 has a different inner diameter or different length, insufflation can be performed at a set flow rate, which is a desired flow rate. Therefore, a pneumoperitoneum apparatus 2 having good operability, the pneumoperitoneum apparatus 2 reducing the trouble of insufflation flow rate adjustment by a user can be provided.

Also, according to the present embodiment, if a measured flow rate is not 0, flow rate adjustment is performed via the flow rate adjusting section 43, an adjustment value for the flow rate adjusting section 43 when the measured flow rate is equal to a set flow rate is stored in the adjustment value storing section 53*a*, and subsequently, when the measured flow rate becomes 0, the flow rate adjustment via the flow rate adjusting section 43 is stopped and the adjustment value read from the adjustment value storing section 53*a* is set for the electro-pneumatic proportional valve 43*a* in the flow rate adjusting section 43, and thus, next time flow rate adjustment is started, the flow rate adjustment can be performed using the adjustment value stored in the adjustment value storing section 53*a*, as an initial value.

Note that although the present embodiment has been described in terms of a case where the flow rate adjusting section 43 is formed using the electro-pneumatic proportional valve 43*a*, the flow rate adjusting section 43 is not limited to the electro-pneumatic proportional valve 43*a* and may be any adjustment valve capable of adjusting a flow rate via an electric signal.

Second Embodiment

Next, a second embodiment of the present invention will be described. In the present embodiment, if, at a fixed time interval, a measured flow rate varies beyond a threshold value, more specifically, a measured flow rate decreases beyond a threshold value, it is detected that an insufflation button 19 in a flexible endoscope 5 is turned off from on, and flow rate adjustment operation of a flow rate adjusting section 43 is stopped.

Thus, in the present embodiment, the CPU 51 in the first embodiment includes a variation amount determining section (variation amount determiner) 51*b* or a flow rate variation amount determining section (flow rate variation amount determiner) 51*b* (indicated by the dotted line in FIG. 3) that acquires a measured flow rate from the flow rate sensor 46 at a fixed time interval $\Delta t$ and determines whether or not an amount of variation of the measured flow rate at the fixed time interval $\Delta t$ decreases beyond a threshold value Fth. Then, if a result of the determination indicates that the variation amount decreases beyond the threshold value Fth, the variation amount determining section 51*b* including a comparison circuit in the CPU 51 stops flow rate adjustment operation of the electro-pneumatic proportional valve 43*a* in the flow rate adjusting section 43.

In the first embodiment, as described with reference to FIG. 7, immediately after the insufflation button 19 is turned off, flow rate adjustment operation of the electro-pneumatic proportional valve 43*a* is not stopped, and thus the adjustment value is varied and thus the insufflation pressure setting value also varies.

Immediately after the insufflation button 19 is turned off from on, the endoscope insufflation conduit 37 is brought into a closed state from an open state and thus the insufflation flow rate varies so as to sharply decrease. An object of the present embodiment is to detect or determine a variation in which an insufflation flow rate sharply decreases immediately after the insufflation button 19 is turned off from on, via the variation amount determining section 51*b*, and promptly stop flow rate adjustment operation of the flow rate adjusting section 43.

Thus, the threshold value Fth is set so that the threshold value Fth enables detection of variation of a measured flow rate to around a set flow rate in a time interval of t3 to t4 in FIG. 7. In other words, where $\Delta t$ is a short time interval of measurement of an insufflation flow rate by the flow rate sensor 46, the threshold value Fth is set to a value that is slightly smaller than a value of $Fs \times \Delta t/(t4-t3)$. Here, Fs is a value of a set flow rate. The rest of the configuration is similar to that of the first embodiment, and thus description thereof will be omitted.

Figure 8:
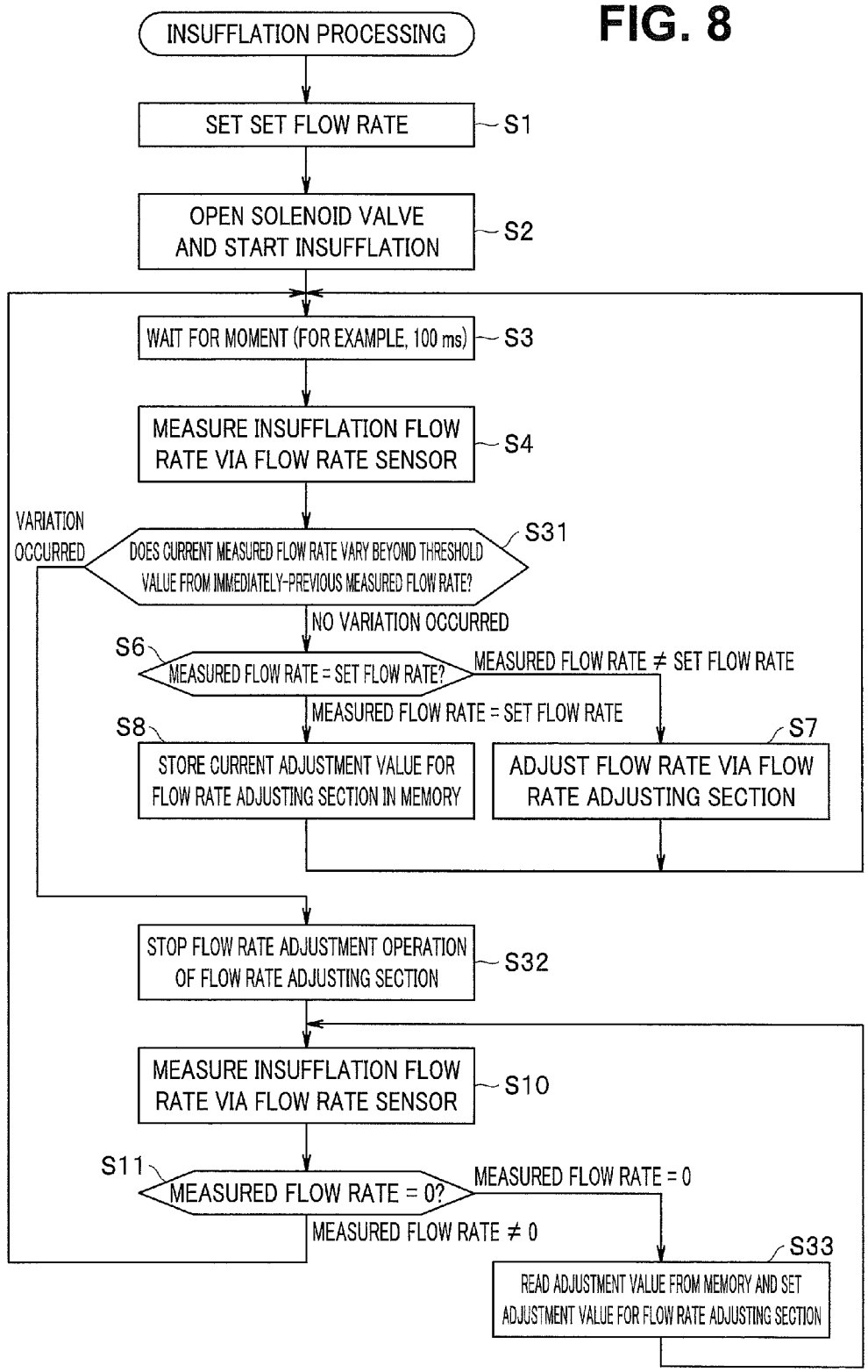
FIG. 8 is a flowchart illustrating a procedure for insufflation processing in a pneumoperitoneum apparatus according to a second embodiment of the present invention.

FIG. 8 illustrates insufflation processing in the present embodiment. The insufflation processing illustrated in FIG. 8 is only partly different from the insufflation processing in FIG. 5, and thus only the different parts will be described. Contents of the insufflation processing in FIG. 8 include change of the processing in step S5 in FIG. 5 to the processing in step S31 and change of the processing in steps S9 to S11 in FIG. 5 to the processing in steps S32, S10, S11 and S33.

As illustrated in FIG. 8, in steps S1 to S4, processing that is similar to that in FIG. 5 is performed, and in step S31 subsequent to the processing in step S4, (the variation amount determining section 51*b*) in the CPU 51 determines whether or not a current measured flow rate measured by the flow rate sensor 46 varies so as to decrease beyond the threshold value Fth from the measured flow rate measured immediately before ($\Delta t$ before). When the insufflation button 19 is on, the measured flow rate does not vary so as to decrease beyond the threshold value Fth. Then, if the (variation amount determining section 51*b* in) the CPU 51 determines that no variation has occurred, the processing proceeds to the processing in step S6 and the processing described with reference to FIG. 5 is performed. Then, flow rate adjustment processing is performed so that the measured flow rate becomes equal to the set flow rate.

In the state in which the measured flow rate is equal to the set flow rate, sufficient pneumoperitoneum is provided inside a digestive organ 4 using insufflation gas, and in order to stop the insufflation, a user turns the insufflation button 19 off from on. In this case, as indicated in FIGS. 7 and 9, the measured flow rate sharply decreases.

Then, in the determination processing in step S31, a result of the determination indicates that a variation in which the measured flow rate decreases beyond the threshold value Fth has occurred, and in the case of this determination result, the processing proceeds to the processing in step S32, and in step S32, the CPU 51 stops the insufflation flow rate adjustment operation performed via the electro-pneumatic proportional valve 43*a* in the flow rate adjusting section 43.

Figure 9:
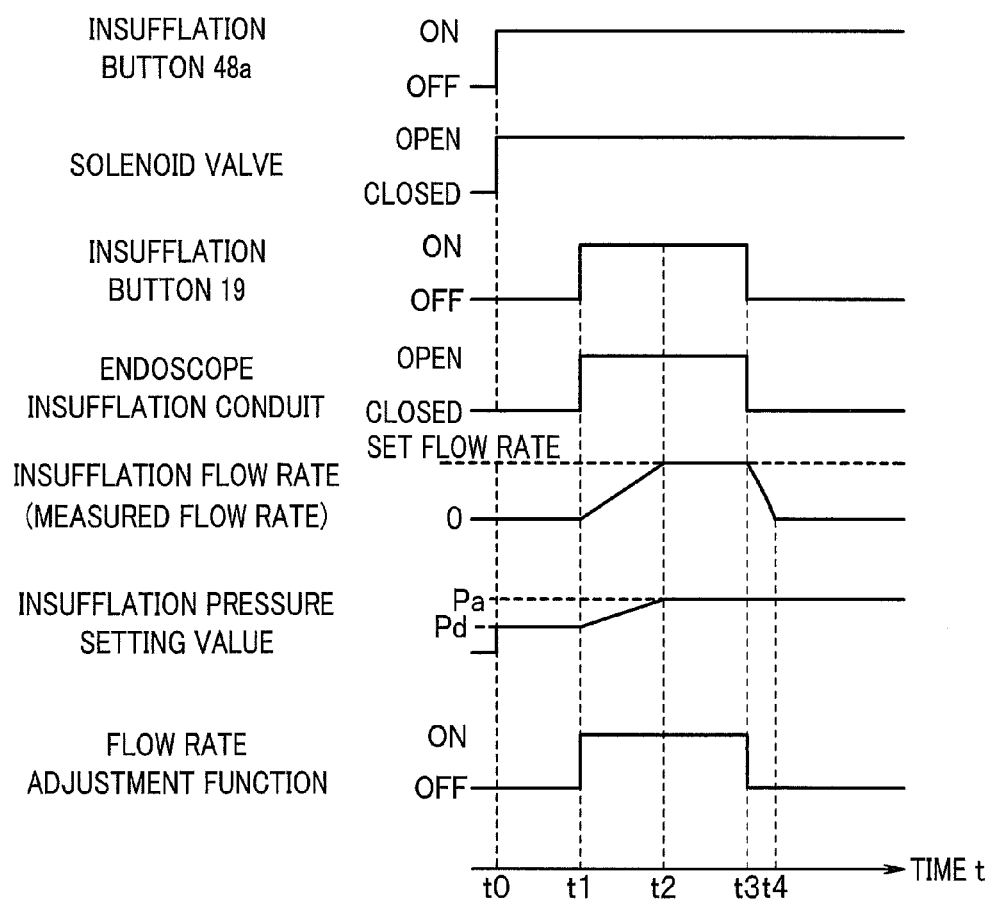
FIG. 9 is a timing chart indicating operation of the pneumoperitoneum apparatus according to the second embodiment.

FIG. 9 illustrates a timing chart in the present embodiment. The timing chart in FIG. 9 is different from the timing chart in FIG. 7 only in terms of operation in a period of time t3 to t4. As described above, a variation in which the measured flow rate sharply decreases immediately after the time t3 is determined (detected) by the variation amount determining section 51*b*, and the CPU 51 stops the insufflation flow rate adjustment operation performed via the electro-pneumatic proportional valve 43*a*.

Thus, the phenomenon of an insufflation pressure setting value, which is to be an adjustment value, increasing immediately after the time t3 in FIG. 7 is stopped in FIG. 9, and the insufflation pressure setting value, which is an adjustment value, does not vary immediately after the time t3.

In step S10 following the processing in step S32 in FIG. 8, the flow rate sensor measures the insufflation flow rate and the CPU 51 acquires the measured flow rate. Then, in next step S11, the CPU 51 determines whether or not the measured flow rate is 0, and if the measured flow rate is 0, in step S33, as in step S9 in FIG. 5, an adjustment value is read from the memory 53, and the read adjustment value is set for the electro-pneumatic proportional valve 43a in the flow rate adjusting section 43. Subsequently, the processing returns to the processing in step S10. Then, the CPU 51 waits for the measured flow rate to becomes a value that is not 0. After the insufflation button 19 being turned off, upon the user turning the insufflation button 19 on from off in order to start insufflation again, in step S11, the CPU 51 determines that the measured flow rate is not 0, and resumes flow rate adjustment operation of the flow rate adjusting section 43 and returns to the processing in step S3.

In the first embodiment, as indicated in FIG. 7, during a period of t4–t1 from the time t1 at which the insufflation button 19 is turned on to the time t4 at which the measured flow rate becomes 0 after the insufflation button 19 being turned off from on, the flow rate adjustment function that performs flow rate adjustment operates.

On the other hand, in the present embodiment, as indicated in FIG. 9, during a period of t3–t1 from a time t1 at which the insufflation button 19 is turned on to the time t3 at which the insufflation button 19 is turned off from on, the flow rate adjustment function that performs flow rate adjustment operates.

The present embodiment provides effects similar to those of the first embodiment and can eliminate unnecessary flow rate adjustment immediately after the insufflation button 19 being turned off from on.

Note that although the above description indicates that the variation amount determining section 51b in the CPU 51 stops flow rate adjustment operation of the electro-pneumatic proportional valve 43a in the flow rate adjusting section 43 only if a determination result indicates that an amount of variation (difference) of a measured flow rate after a time interval of Δt decreases beyond a positive threshold value Fth, the threshold value Fth may be set as a positive/negative value to determine whether or not there is a variation beyond the threshold value. For example, it is possible that if an amount of variation (difference) of the measured flow rate after a time interval of Δt goes beyond ±Fth, flow rate adjustment operation is stopped.

More specifically, the threshold value may be set to ±Fth=±0.5 L/min. However, the threshold value should be set to a value not including the variation that is the increase of the measured flow rate during a period of the time t1 to t2 in FIG. 7.

Third Embodiment

Next, a third embodiment of the present invention will be described. In the present embodiment, a flow rate correction button (or a flow rate adjusting button) 48c is provided in, for example, the touch panel 48 in the first embodiment to, before a procedure such as a surgical operation, correct an adjustment value for the flow rate adjusting section 43 to an adjustment value suitable for a flexible endoscope 5 used for the procedure so that flow rate adjustment processing during the procedure can smoothly be performed.

Figure 10:
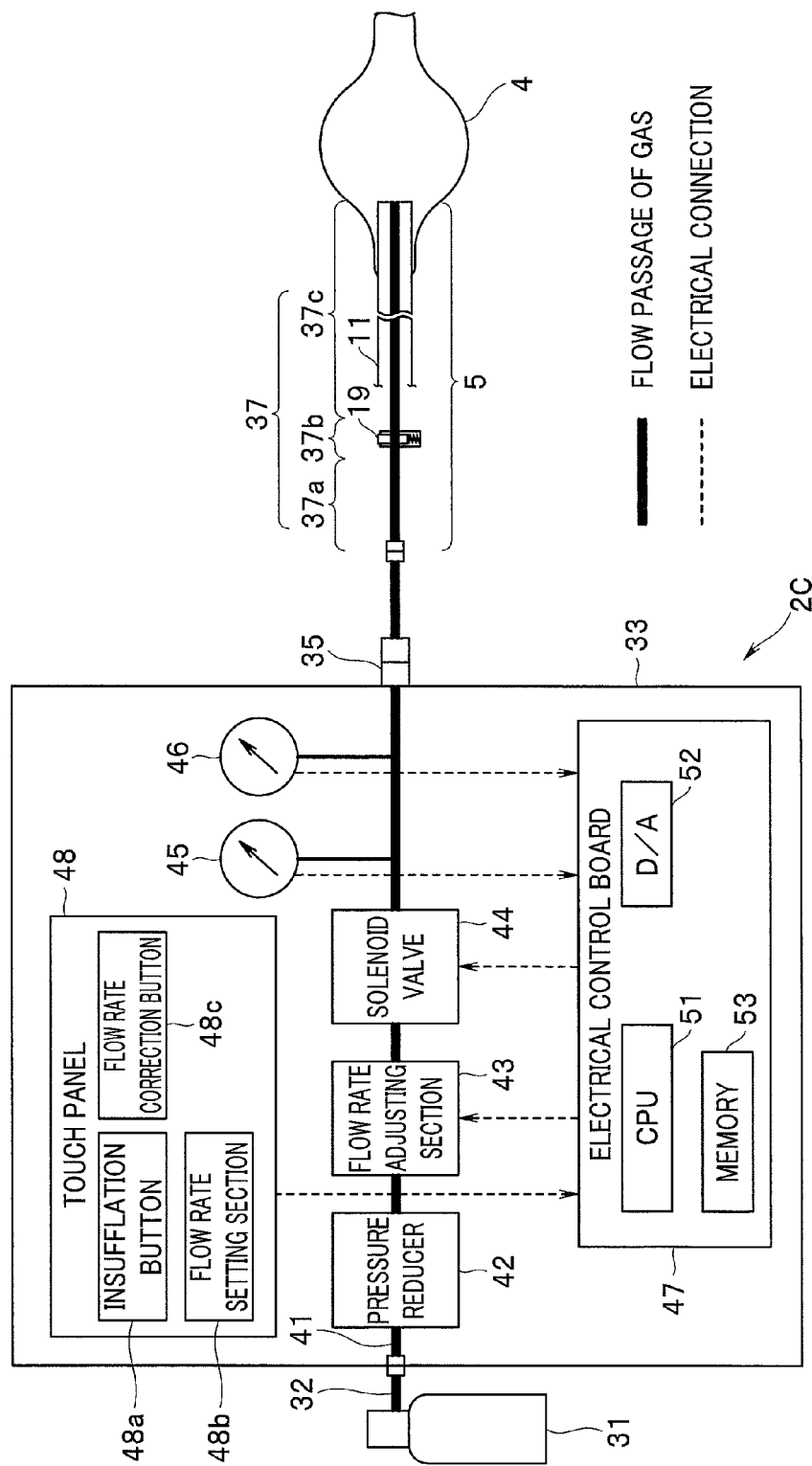
FIG. 10 is a diagram illustrating a configuration of a pneumoperitoneum apparatus according to a third embodiment of the present invention.

FIG. 10 illustrates a pneumoperitoneum apparatus 2C according to the present embodiment. The pneumoperitoneum apparatus 2C is configured by further providing a flow rate correction button 48c in the touch panel 48 in the pneumoperitoneum apparatus 2 in FIG. 2, and an operation signal generated upon the flow rate correction button 48c being operated is inputted to a CPU 51.

In the present embodiment, when the flow rate correction button 48c is operated, the CPU 51 detects that the flow rate correction button 48c is operated, and performs flow rate correction processing or flow rate adjustment processing via the flow rate adjusting section 43. Then, the CPU 51, which provides a control section, performs control so that an adjustment value when a measured flow rate is equal to a set flow rate as a result of flow rate correction processing or flow rate adjustment processing is stored in an adjustment value storing section 53a in a memory 53, and subsequently performs control so that when the flow rate adjusting section 43 actually starts flow rate adjustment, the adjustment value stored in the adjustment value storing section 53a is used.

The rest of the configuration is similar to that of the first embodiment, and description thereof will be omitted. The flow rate correction button 48c provides a flow rate adjustment operation section (or a flow rate adjustment operation device) for performing an operation to cause the flow rate adjusting section 43, which is an insufflation flow rate adjusting section, to start operation of adjusting an insufflation flow rate of insufflation to an endoscope insufflation conduit 37.

Figure 11:
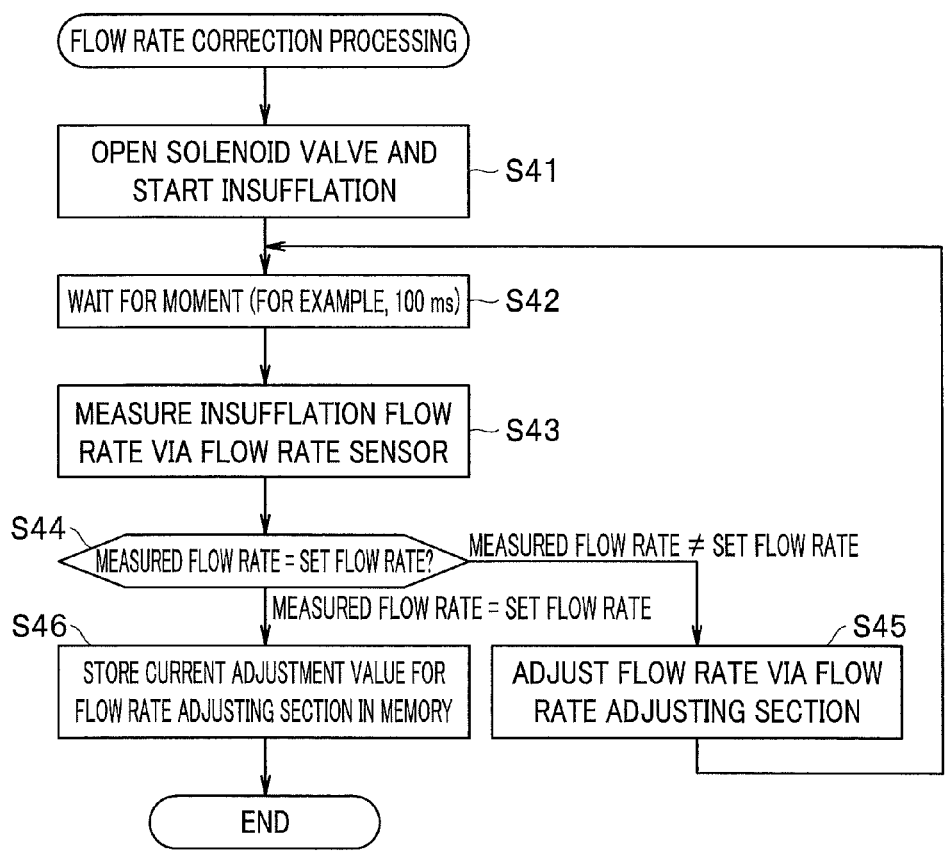
FIG. 11 is a flowchart illustrating processing for flow rate correction when a flow rate correction button is operated.

FIG. 11 illustrates flow rate correction processing when the flow rate correction button 48c is operated.

Here, when a user operates the flow rate correction button 48c, the user operates the flow rate correction button 48c before the user inserts a flexible endoscope 5 into a body cavity of a patient 3. The flow rate correction processing illustrated in FIG. 11 is similar to the processing in steps S1 to S8 in FIG. 5. Also, the description will be provided assuming that a set flow rate is set in advance by the user before the user operates the flow rate correction button 48c.

Upon the flow rate correction button 48c being operated, in first step S41, the CPU 51 opens a solenoid valve 44 and starts insufflation operation. Also, the user also turns an insufflation button 19 on. In next step S42, the CPU 51 waits for a moment (for example, 100 ms).

After a lapse of a moment, as indicated in step S43, a flow rate sensor 46 measures an insufflation flow rate. Then, the CPU 51 acquires the insufflation flow rate measured by the flow rate sensor 46, as a measured flow rate.

In next step S44, the CPU 51 determines whether or not the measured flow rate is equal to the set flow rate. In the current operation status, the measured flow rate has not reached the set flow rate, the CPU 51 determines that the measured flow rate is not equal to the set flow rate, and in next step S45, the CPU 51 performs control so that an electro-pneumatic proportional valve 43a in the flow rate adjusting section 43 performs flow rate adjustment. For the flow rate adjustment processing, the processing in steps S21 and S22 in FIG. 6 is performed and the processing returns to the processing in step S42.

As a result of the above-described control loop, an adjustment value increases in a stepwise manner, whereby the measured flow rate also increases in a stepwise manner and reaches the set flow rate. Then, in step S44, the CPU 51 determines that the measured flow rate becomes equal to the set flow rate, and proceeds to the processing in step S46. In step S46, the CPU 51 stores the adjustment value when the measured flow rate is equal to the set flow rate, in the memory 53 and ends the flow rate correction processing in FIG. 11.

The flow rate correction processing in FIG. 11 enables pneumoperitoneum with an initial value (default setting value) of an adjustment value when the electro-pneumatic proportional valve 43a in the flow rate adjusting section 43 starts flow rate adjustment operation, smoothly set to a set flow rate, compared to a case where flow rate correction processing is not performed.

Figure 12:
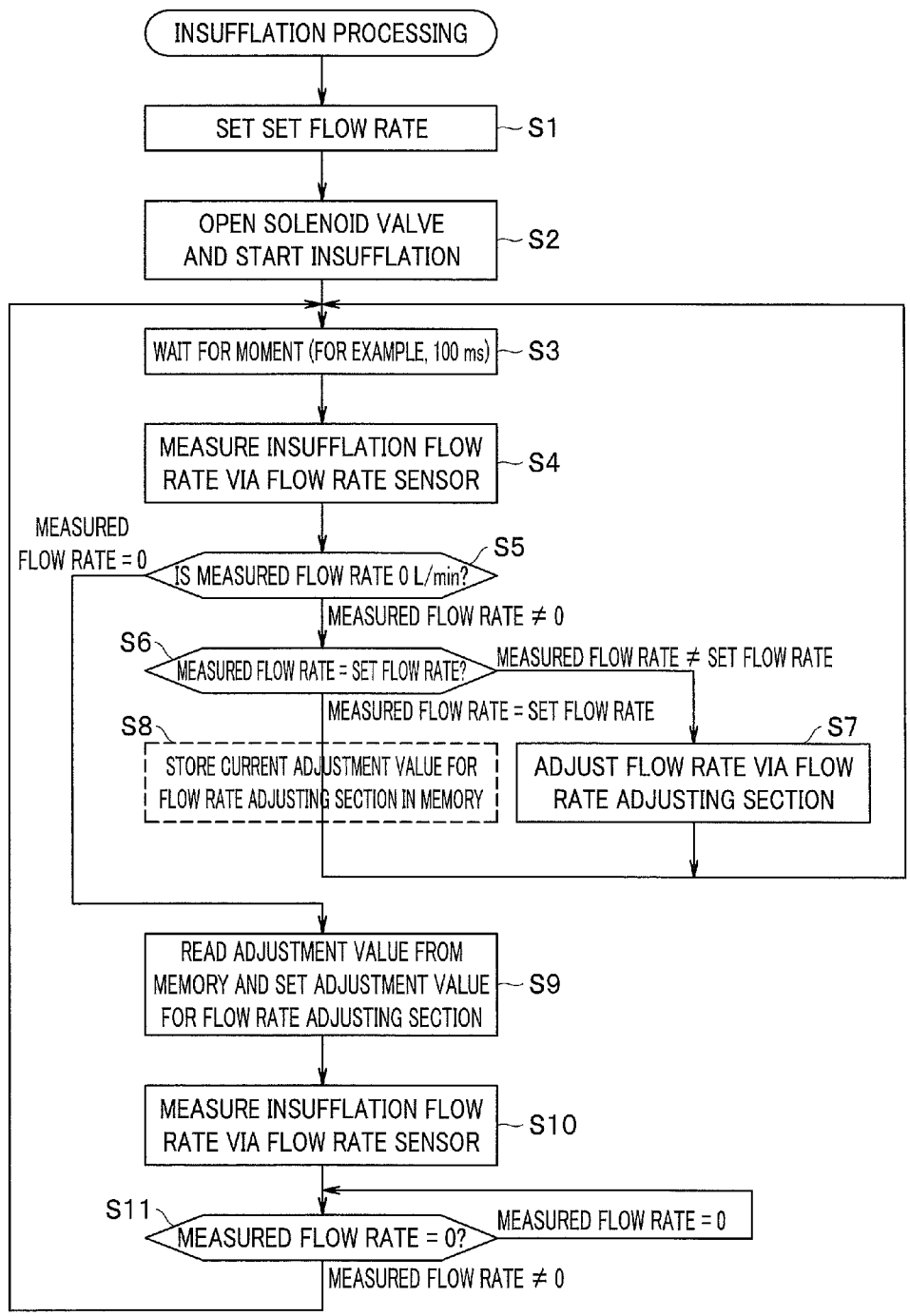
FIG. 12 is a flowchart illustrating a procedure for insufflation processing in the pneumoperitoneum apparatus according to the third embodiment.

After the flow rate correction processing is performed as described above, an insertion portion 11 of the flexible endoscope 5 is inserted into the body cavity of the patient 3, for example, a digestive organ 4, and the insufflation button 48a is operated to start insufflation in an actual procedure. FIG. 12 illustrates insufflation processing in the present embodiment. The flowchart illustrated in FIG. 12 includes the content of the insufflation processing in FIG. 5 with the processing in step S8 omitted. Thus, in FIG. 12, the omitted processing in step S8 in the insufflation processing in FIG. 5 is indicated by the dotted line.

As described above, in the present embodiment, an adjustment value when a measured flow rate is equal to a set flow rate as a result of flow rate correction processing is stored in the memory 53, and thus, processing for storing the adjustment value in the memory 53 is not performed in the insufflation processing in FIG. 12. The rest of the processing is similar to that of the case in FIG. 5.

According to the present embodiment, the effects of the first embodiment are provided, and furthermore, before an actual procedure, an adjustment value for the flow rate adjusting section 43 to start flow rate adjustment operation is set to a set flow rate by means of flow rate correction processing using an flexible endoscope 5 to be used for the procedure, and thus, when an actual procedure is performed using the flexible endoscope 5, pneumoperitoneum can smoothly be provided with an insufflation flow rate (measured flow rate) set to the set flow rate.

Note that, instead of flow rate correction such as described above, it is possible to acquire, from a flexible endoscope 5 to be actually connected and used, or a video processor 7, endoscope information including information on an endoscope insufflation conduit 37 of the flexible endoscope 5 and set an adjustment value based on the information on the endoscope insufflation conduit 37 in the acquired endoscope information.

Fourth Embodiment

Next, a fourth embodiment of the present invention will be described. In the first embodiment, after a measured flow rate reaches a set flow rate, when the insufflation button 19 is turned off from on and the measured flow rate decreases from the set flow rate to 0, flow rate adjustment operation is stopped. In the present embodiment, after a measured flow rate reaches a set flow rate, during decrease from the set flow rate to 0, if the measured flow rate varies to a value that is equal to or below a threshold value that is larger than 0, flow rate adjustment operation is stopped.

Thus, in the present embodiment, a CPU 51 has a function of a flow rate determining section (or a flow rate determiner) 51c (indicated by a dotted line in FIG. 15 described later) that determines whether or not a measured flow rate measured by a flow rate sensor 46 varies to a value that is equal to or below a threshold value (or decreases to a value that is equal to or below a threshold value), and if a result of the determination indicates that the measured flow rate varies to be a value that is equal to or below the threshold value, performs control to stop flow rate adjustment operation of a flow rate adjusting section 43. The rest of the configuration is similar to that of the first embodiment, and thus description thereof will be omitted.

Figure 13:
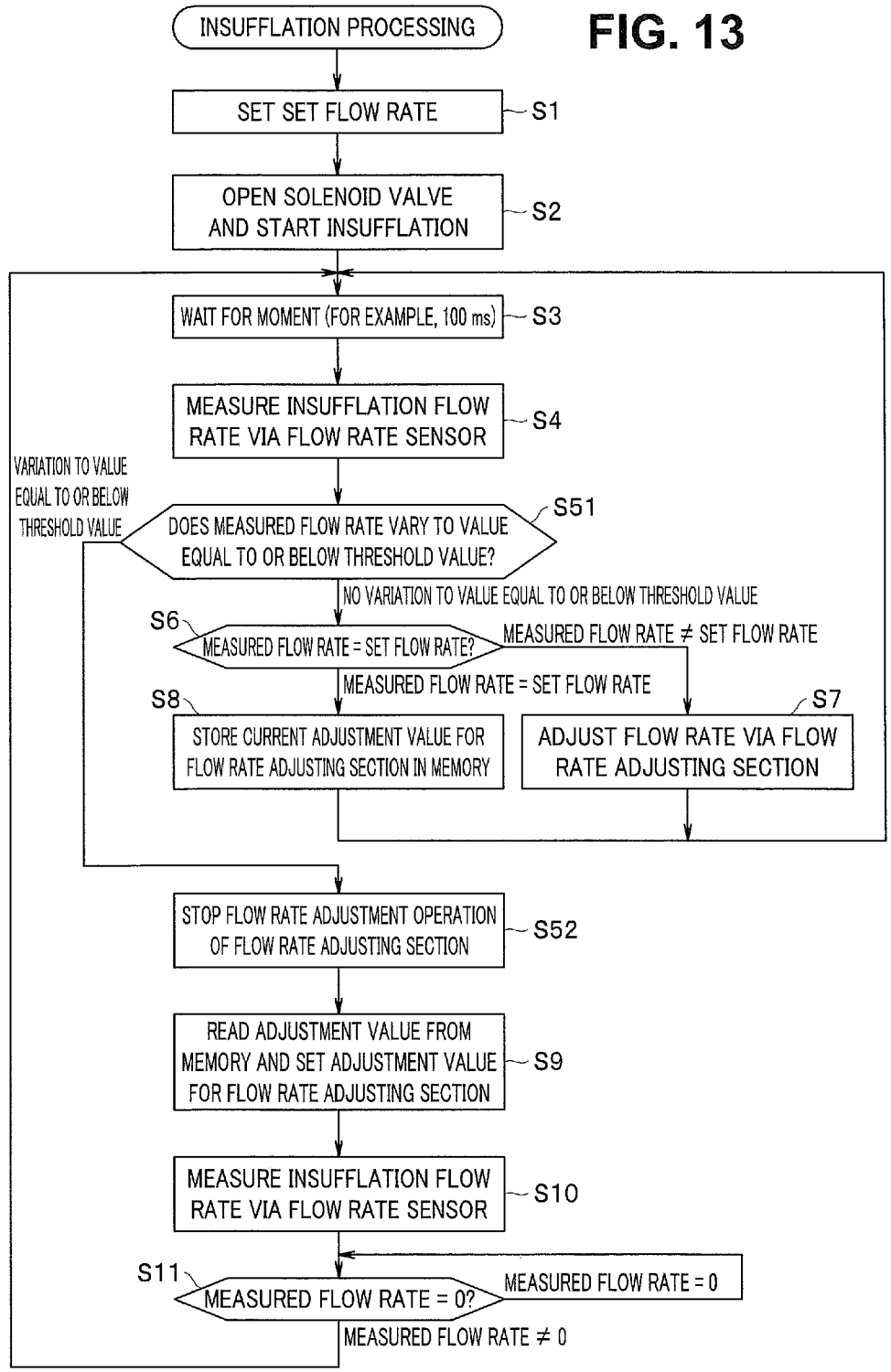
FIG. 13 is a flowchart illustrating a procedure for insufflation processing in a pneumoperitoneum apparatus according to a fourth embodiment of the present invention.

FIG. 13 illustrates content of insufflation processing in the present embodiment. The insufflation processing in FIG. 13 is only partly different from the insufflation processing in FIG. 5, and only the different parts will be described. Contents of the insufflation processing in FIG. 13 include change of the processing in step S5 in FIG. 5 to the processing in step S51 and insertion of the processing in step S52 before the processing in step S9 in FIG. 5.

As illustrated in FIG. 13, in steps S1 to S4, processing similar to that in FIG. 5 is performed, in step S51 following the processing in step S4, (the flow rate determining section 51c) in the CPU 51 determines whether or not a current measured flow rate measured by the flow rate sensor 46 varies to a value that is equal to or below a threshold value. In the current operation status, the measured flow rate increases, the CPU 51 determines that the measured flow rate does not vary to a value that is equal to or below the threshold value.

In the case of this determination result, the processing proceeds to step S6, and as described with reference to FIG. 5, the flow rate adjusting section 43 performs flow rate adjustment according to the flow rate adjustment control loop returning to step S3 through step S7. Then, after the adjustment of the measured flow rate to be equal to the set flow rate, the processing proceeds from step S6 to the processing in step S8, and after the processing in step S8, returns to the processing in step S3, and processing is performed according to a loop of steps S3, S4, S51, S6 and S8.

Insufflation is performed in a state in which the measured flow rate is equal to the set flow rate, and when sufficient pneumoperitoneum is provided inside a digestive organ 4, a user turns an insufflation button 19 off from on. Then, as indicated in the timing chart in FIG. 14, the measured flow rate measured by the flow rate sensor 46 sharply decreases, and for example, at a time t5, the measured flow rate decreases to a value that is equal to or below the threshold value and then becomes 0 at a time t4.

In this case, in step S51, (the flow rate determining section 51c in) the CPU 51 determines that the current measured flow rate measured by the flow rate sensor 46 varies to a value that is equal to or below the threshold value, and the processing proceeds to the processing in step S52. In step S52, the CPU 51 stops the flow rate adjustment operation of the flow rate adjusting section 43. Furthermore, in step S9, the CPU 51 reads an adjustment value from a memory 53 and sets the adjustment value for the flow rate adjusting section 43.

Figure 14:
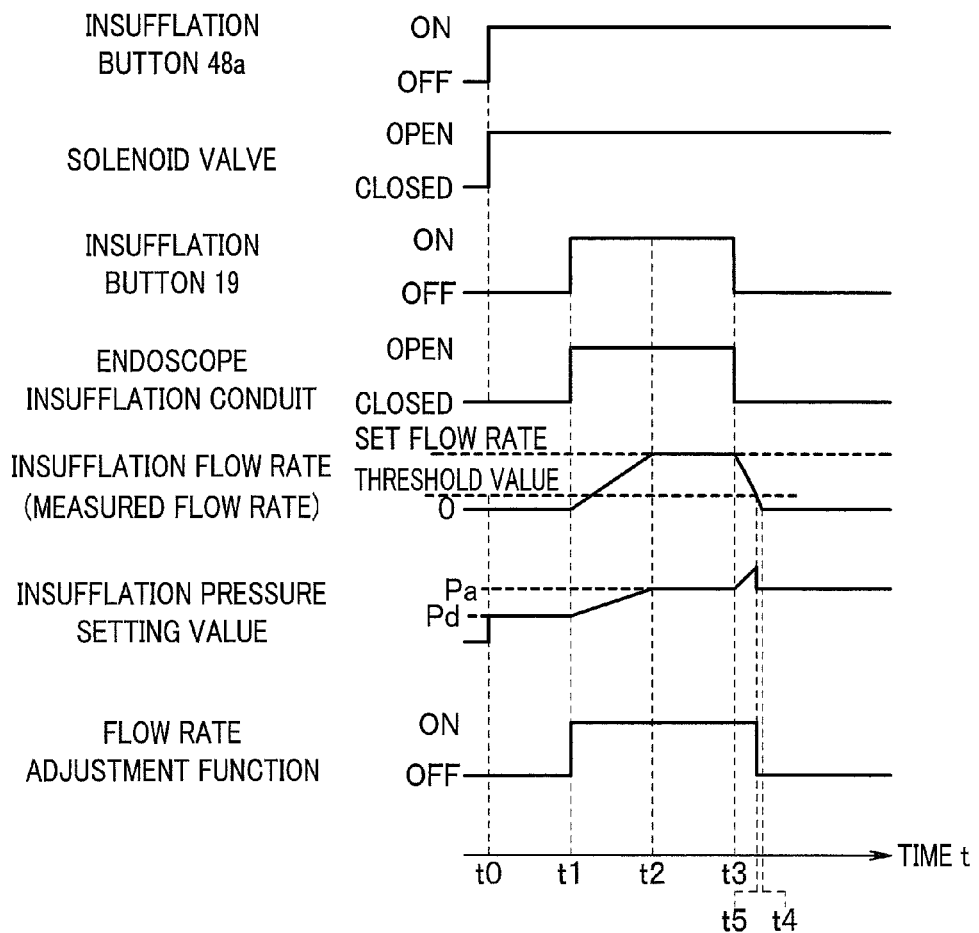
FIG. 14 is a timing chart indicating operation of the pneumoperitoneum apparatus according to the fourth embodiment.

Thus, as indicated in the timing chart in FIG. 14, during a period of time t3 to t5, the flow rate adjusting section 43 performs flow rate adjustment operation, and thus, as in the case in FIG. 5, an insufflation pressure setting value rises. However, at the time t5, the flow rate adjustment operation of the flow rate adjusting section 43 is stopped, and as a result of the processing in step S9, the insufflation pressure setting value becomes a value corresponding to the adjustment value when the measured flow rate is the set flow rate.

After the processing in step S9, in step S10, an insufflation flow rate is measured by the flow rate sensor 46, and the CPU 51 acquires the insufflation flow rate as a measured flow rate. In next step S11, the CPU 51 determines whether or not the measured flow rate is 0, and if the measured flow rate is 0, continues the processing in step S11.

When the user wishes to perform insufflation again after turning the insufflation button 19 off, the user turns the insufflation button 19 on from off. Then, in step S11, the CPU 51 determines that the measured flow rate is not 0 and starts flow rate adjustment operation of the flow rate adjusting section 43 and returns to the processing in step S3.

The timing chart in FIG. 14 is different from the timing chart in FIG. 7 only in terms of a period immediately before the time t4 (period of time t5 to t4 in FIG. 14).

Although in the first embodiment, when the insufflation button 19 is turned off from on, unnecessary flow rate adjustment is performed from the time t3 at which the insufflation button 19 is turned off to the time t4 at which the measured flow rate becomes 0, in the present embodiment, the period of the unnecessary flow rate adjustment can be reduced to a period from the time t3 to the time t5 preceding the time t4 at which the measured flow rate becomes 0. Thus, in the present embodiment, a period in which the flow rate adjustment function operates is a period of time t1 to t5.

According to the present embodiment, the effects of the first embodiment are provided, and also an operation period in which unnecessary flow rate adjustment is performed when the insufflation button 19 is turned off from on can be reduced. Here, if the threshold value is set to a value that is slightly larger than 0, operation and effects that are substantially similar to those of the first embodiment are provided.

In order to more promptly detect or determine a timing of the insufflation button 19 being turned off from on, the threshold value to be used by the flow rate determining section for the determination may be set to a value that is, for example, around 80% to 90% of, for example the set flow rate. In this case, a timing of the insufflation button 19 being turned off from on when the measured flow rate is the set flow rate can be detected with a short time lag.

Fifth Embodiment

Next, a fifth embodiment of the present invention will be described. In the above-described first to fourth embodiments, it is detected (determined) based on the measured flow rate from the flow rate sensor 46 that the insufflation button 19 is turned off from on, flow rate adjustment performed via the flow rate adjusting section 43 is stopped, and furthermore, the adjustment value read from the memory 53 is set for the flow rate adjusting section 43.

On the other hand, in the present embodiment, a pressure when an endoscope insufflation conduit 37 is closed as a result of an insufflation button 19 being turned off from on is detected or determined using a measured pressure measured by a pressure sensor 45.

In other word, when the endoscope insufflation conduit 37 is closed as a result of the insufflation button 19 being turned off from on, a lock pressure value Plo, which is a measured pressure value or a pressure measurement value in a closed state measured by the pressure sensor 45 is detected or determined, and if the lock pressure value Plo is detected or determined, the CPU 51 stops flow rate adjustment performed via a flow rate adjusting section 43.

Figure 15:
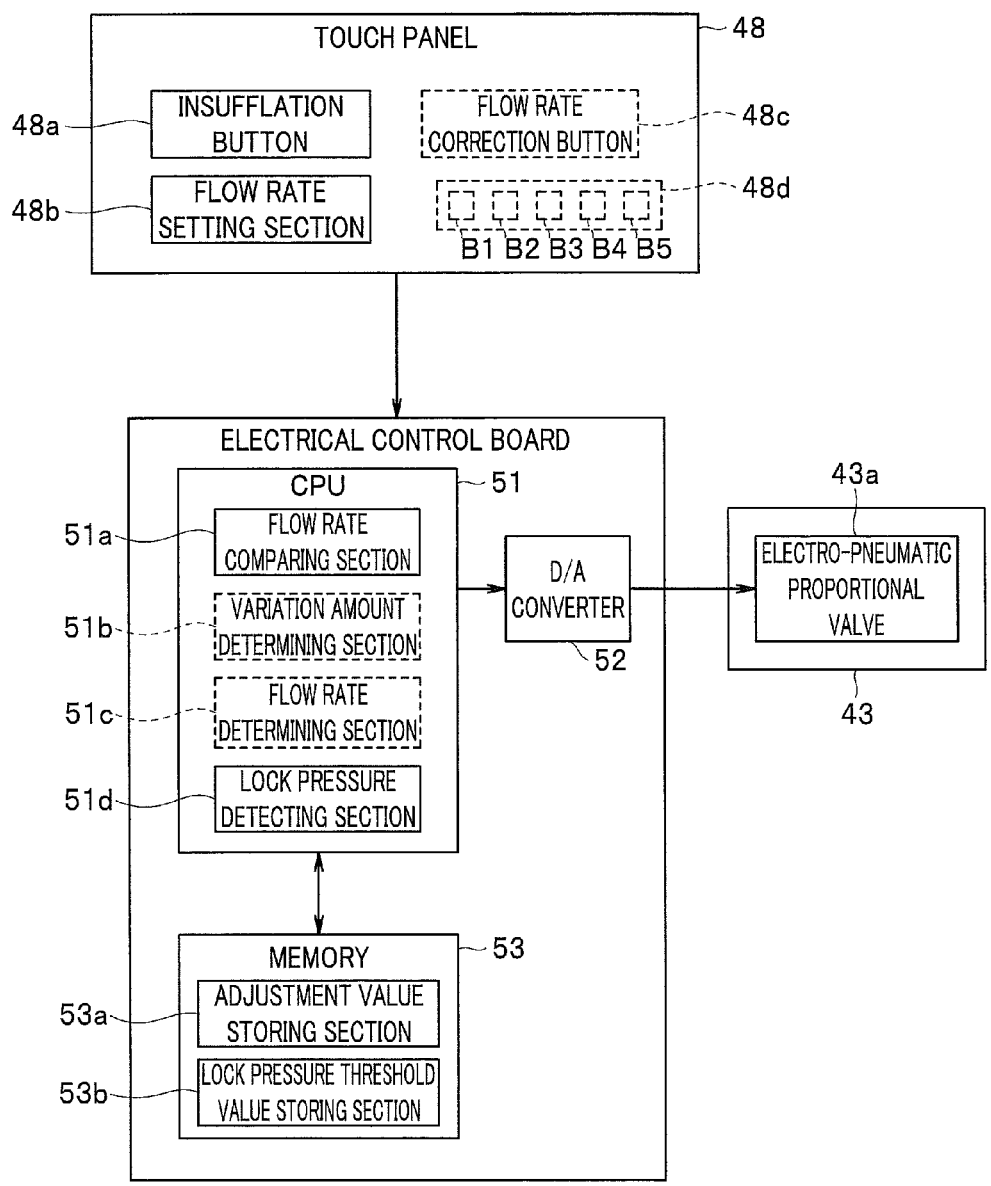
FIG. 15 is a diagram illustrating a configuration of a pneumoperitoneum apparatus according to a fifth embodiment of the present invention.

Thus, a pneumoperitoneum apparatus according to the present embodiment is the pneumoperitoneum apparatus 2 illustrated in FIG. 2 in which on an electrical control board 47 thereof, for example, as illustrated in FIG. 15, the CPU 51 has a function of a lock pressure detecting section (or a lock pressure detecting circuit) 51*d*.

Also, for example, in order to detect a lock pressure value Plo, a memory 53 includes a lock pressure threshold value storing section (or a lock pressure threshold value storing device) 53*b* that stores a lock pressure threshold value Pth, which is a pressure value that is slightly smaller than the lock pressure value Plo.

Then, (the lock pressure detecting section 51*d* of) the CPU 51 compares the lock pressure threshold value Pth and a measured pressure (pressure measurement value) measured by the pressure sensor 45, and if the measured pressure exceeds the lock pressure threshold value Pth, determines that an insufflation button is in an off state and performs control to stop flow rate adjustment performed via the flow rate adjusting section 43.

Figure 16:
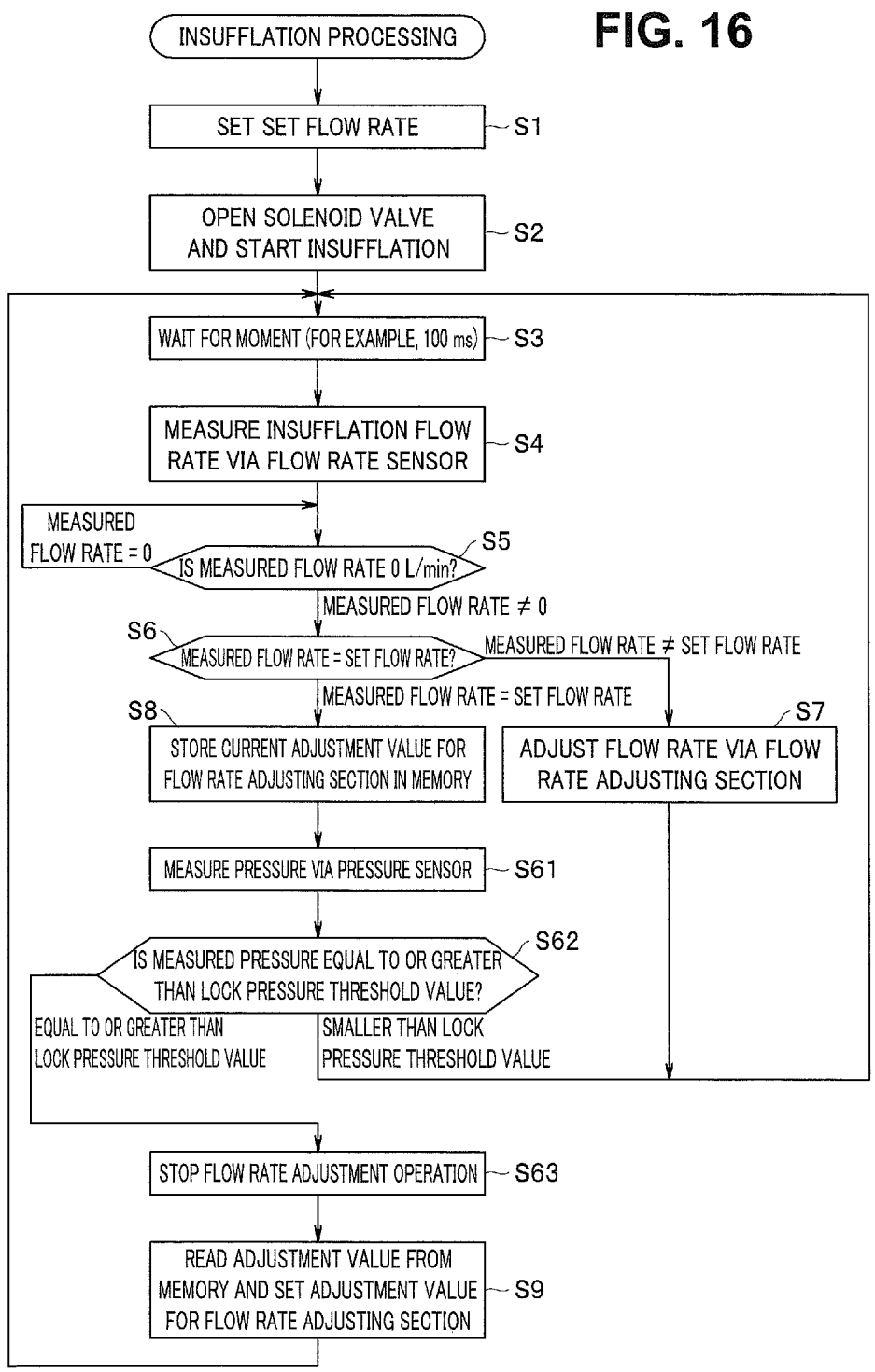
FIG. 16 is a flowchart illustrating a procedure for insufflation processing in the pneumoperitoneum apparatus according to the fifth embodiment.

The rest of the configuration is similar to that of first embodiment. FIG. 16 illustrates insufflation processing according to the present embodiment.

The insufflation processing illustrated in FIG. 16 is only partly different from the insufflation processing in FIG. 5, and thus only the different parts will be described. In the insufflation processing in FIG. 16, the processing in steps S61 and S62 is performed after the processing in step S8 in FIG. 5, and according to a result of determination in step S62, the processing in step S63 is performed, and then the processing in step S9 is performed. Also, the processing in step S5 has been changed so that if a measured flow rate is 0, the measured flow rate becoming a value that is not 0 is waited for.

More specifically, as in the case of FIG. 5, the processing in steps S1 to S5 is performed, and if a measured flow rate is a value that is not 0, the CPU 51 starts flow rate adjustment operation via the flow rate adjusting section 43, and proceeds to next step S6, and as described with reference to FIG. 5, determines whether or not the measured flow rate is equal to a set flow rate.

In this operation status, since the measured flow rate has not reached the set flow rate, in step S7, the flow rate adjusting section 43 slightly increases an adjustment value and then, the processing returns to step S3 and adjustment is made so that the measured flow rate becomes equal to the set flow rate, by repetition of operation similar to the above.

When the measured flow rate becomes equal to the set flow rate, the processing proceeds to the processing in step S8 after the processing in step S6, and the current adjustment value for the flow rate adjusting section 43 is stored in the memory 53, and then, in step S61, an insufflation pressure in an insufflation conduit 41 for pneumoperitoneum is measured by the pressure sensor 45 and the measured pressure (pressure measurement value) measured is acquired by the CPU 51.

In next step S62, the lock pressure detecting section 51*d* of the CPU 51 detects or determines whether or not the measured pressure is equal to or greater than the lock pressure threshold value Pth. In the current operation status, insufflation operation is continued in a state in which the measured flow rate is equal to the set flow rate. Therefore, in step S62, the lock pressure detecting section 51*d* determines that the measured pressure is smaller than the lock pressure threshold value Pth, and the processing returns to the processing in step S3, and a loop of the processing in step S3 to S6, S8, S61 and S62 is repeated.

If a user determines that sufficient pneumoperitoneum is provided inside a digestive organ 4 as a result of insufflation gas being fed into the digestive organ 4 in a state in which the measured flow rate is equal to the set flow rate, the user turns the insufflation button 19 off from on. Upon the insufflation button 19 being turned off, in step S62, the lock pressure detecting section 51*d* detects or determines that the measured pressure is equal to or greater than the lock pressure threshold value Pth, the processing proceeds to the processing in step S63, and in step S63, the CPU 51 stops the flow rate adjustment operation of the flow rate adjusting section 43. After the processing in step S63, as indicated in step S9, the CPU 51 reads the adjustment value from the memory 53 and sets the adjustment value for the flow rate adjusting section 43 and then returns to the processing in step S3.

Figure 17:
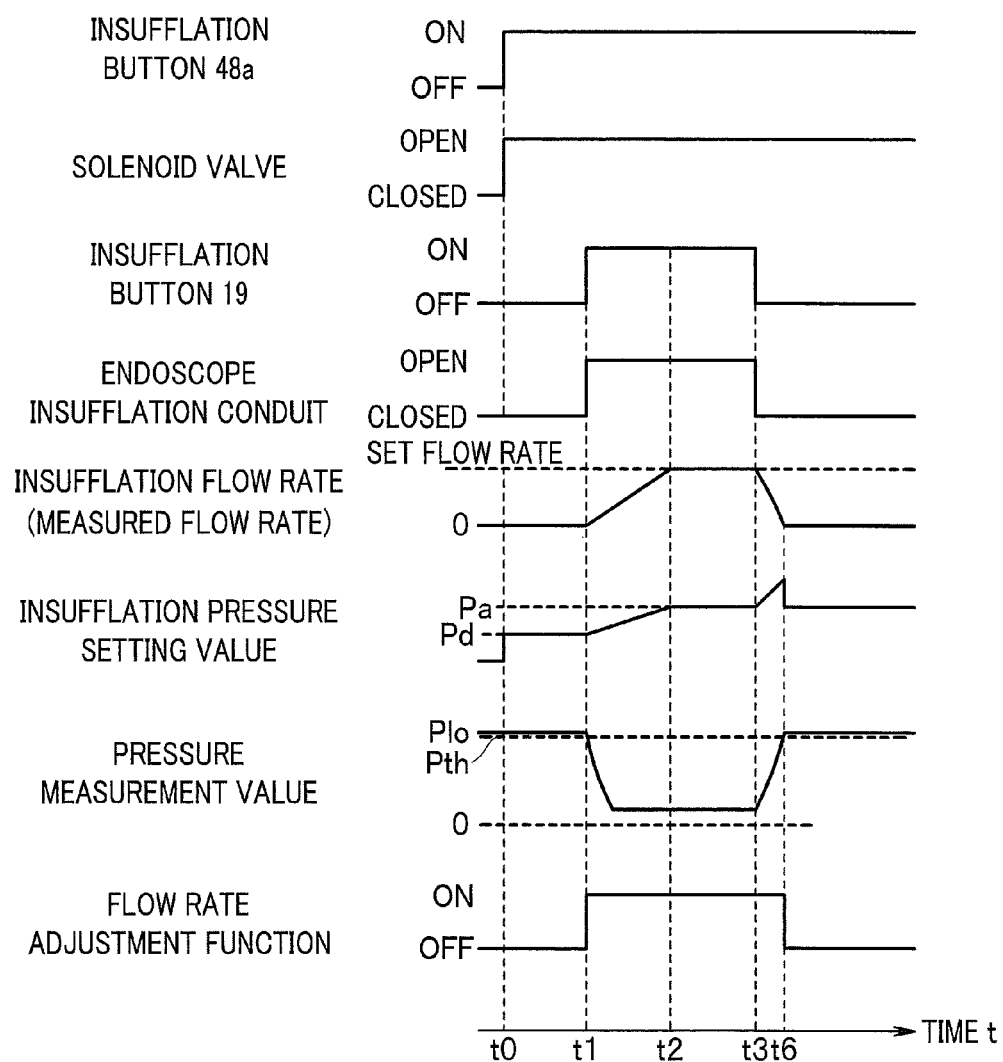
FIG. 17 is a timing chart indicating operation of the pneumoperitoneum apparatus according to the fifth embodiment.

FIG. 17 is a timing chart of operation of the present embodiment. The timing chart in FIG. 17 is the timing chart in FIG. 7 with the addition of the content that whether or not a pressure measurement value measured by the pressure sensor 45 is equal to or greater than the lock pressure threshold value Pth is determined.

As illustrated in FIG. 17, after an insufflation flow rate (measured flow rate) reaches a set flow rate subsequent to the insufflation button 19 being turned on, at a time t6 at which a measured pressure measured by the pressure sensor 45 becomes equal to or greater than the lock pressure threshold value Pth, as indicated in steps S62 and S63 in FIG. 16, the CPU 51 stops flow rate adjustment operation of the flow rate adjusting section 43, and as indicated in step S9, reads an adjustment value from the memory 53 and sets the adjustment value for the flow rate adjusting section 43.

Thus, where, for example, the time t6 is regarded as t4 in FIG. 7, the operation is substantially similar to the operation of the first embodiment.

Therefore, the present embodiment provides effects that are substantially the same as those of the first embodiment.

Note that in the present embodiment, as indicated in dotted lines in a touch panel 48 illustrated in FIG. 15, selection buttons (or selection switches) 48d may be provided to enable selection of any of operation modes of the above-described first to fifth embodiments by selectively turning on a relevant one of first to fifth buttons B1 to B5 included in the selection buttons 48d.

A characterizing part of the operation modes of the first, second, fourth and fifth embodiments except the third embodiment is detection means for detecting that the insufflation button 19 provided in the flexible endoscope 5 is turned off from on (in other words, the endoscope insufflation conduit 37 is brought into a closed state from an open state). The first button B1, the second button B2, the fourth button B4 and the fifth button B5 provide selection switches for selection from a plurality of detection operations (modes) to detect operation for second switching to switch the endoscope insufflation conduit 37 from an open state to a closed state via the insufflation button 19.

Also, in order to enable execution of a selected operation mode, a flow rate correction button 48c, which is indicated by a dotted line, is provided in the touch panel 48. Also, the CPU 51 includes a variation amount determining section 51b as indicated by a dotted line.

Then, if a user turns on, for example, a j-th button Bj (j=any of 1, 2, . . . , 5), the above-described operation of the j-th embodiment is performed.

Provision of the selection buttons 48d to enable selection from a plurality of operation modes as described above enables a user to select an operation mode suitable for a surgical operation, enhancing convenience for the user.

The CPU 51, which provides a control section, performs control according to selection from the selection buttons 48d so that if the CPU 51 determines that a predetermined condition including a first condition that the measured flow rate measured by the flow rate sensor 46, which is a flow rate measuring section, varies to a value that is equal to or below the threshold value is met, operation of adjusting the insufflation flow rate via the flow rate adjusting section 43 is stopped and the adjustment value read from the adjustment value storing section 53a is set for the flow rate adjusting section 43. The predetermined condition in this case may be extended as follows.

A configuration may be made so that, if it is determined that the predetermined condition including the first condition that the measured flow rate measured by the flow rate sensor 46, which is the flow rate measuring section, varies to a value that is equal to or below the threshold value or a second condition that the measured pressure measured by the pressure sensor 45, which is a pressure measuring section, is the lock pressure value Plo is met, the CPU 51, which provides the control section, performs control to stop operation of adjusting the insufflation flow rate via the flow rate adjusting section 43 and set the adjustment value read from the adjustment value storing section 53a for the flow rate adjusting section 43.

Note that an embodiment provided by, e.g., combining parts of the above-described embodiments also falls within the present invention.

What is claimed is:

1. A pneumoperitoneum apparatus comprising:
an insufflation gas source;
an insufflation conduit connected to the insufflation gas source and configured to feed insufflation gas for pneumoperitoneum;
an endoscope connection tube connected to the insufflation conduit and configured to connect the insufflation conduit to an endoscope insufflation conduit provided inside an endoscope;
a flow rate sensor provided on the insufflation conduit and configured to measure an insufflation flow rate as a measured flow rate;
a flow rate setting knob configured to set the insufflation flow rate measured by the flow rate sensor to a set flow rate that is larger than 0;
an electro-pneumatic proportional valve provided on the insufflation conduit and configured so as to, if the measured flow rate measured by the flow rate sensor is not equal to the set flow rate, adjust the insufflation flow rate of insufflation to the endoscope insufflation conduit according to an adjustment value defining an insufflation pressure value;
a memory configured so as to, if the measured flow rate measured by the flow rate sensor is equal to the set flow rate, store the adjustment value; and
a CPU configured so as to, if the measured flow rate measured by the flow rate sensor decreases to or below a threshold value after the measured flow rate reaches the set flow rate, perform control to change the adjustment value,
wherein the threshold value is an insufflation flow rate value that is at least larger than 0.

2. A pneumoperitoneum apparatus comprising:
an insufflation gas source;
an insufflation conduit connected to the insufflation gas source and configured to feed insufflation gas for pneumoperitoneum;
an endoscope connection tube connected to the insufflation conduit and configured to connect the insufflation conduit to an endoscope insufflation conduit provided inside an endoscope;
a flow rate sensor provided on the insufflation conduit and configured to measure an insufflation flow rate as a measured flow rate;
a flow rate setting knob configured to set the insufflation flow rate measured by the flow rate sensor to a set flow rate that is larger than 0;
an electro-pneumatic proportional valve provided on the insufflation conduit and configured so as to, if the measured flow rate measured by the flow rate sensor is not equal to the set flow rate, adjust the insufflation flow rate of insufflation to the endoscope insufflation conduit according to an adjustment value defining an insufflation pressure value;

a memory configured so as to, if the measured flow rate measured by the flow rate sensor is equal to the set flow rate, store the adjustment value; and a CPU configured so as to:
if the measured flow rate measured by the flow rate sensor decreases to or below a threshold value after the measured flow rate reaches the set flow rate, perform control to change the adjustment value, if the measured flow rate measured at a first time by the flow rate sensor varies beyond a predetermined threshold value compared to a measured flow rate value measured at a second time immediately before the first time, perform control to stop operation of the electro-pneumatic proportional valve adjusting the insufflation flow rate, and if the measured flow rate at the first time does not vary beyond the predetermined threshold value, perform control to continue the operation of the electro-pneumatic proportional valve adjusting the insufflation flow rate.

3. The pneumoperitoneum apparatus according to claim 2, further comprising:
a flow rate correction button configured so as to be operated to make the electro-pneumatic proportional valve start operation of adjusting the insufflation flow rate of insufflation to the endoscope insufflation conduit,
wherein:
according to a result of the operation by the electro-pneumatic proportional valve, the memory stores the adjustment value when the measured flow rate measured by the flow rate sensor is equal to the set flow rate; and
the CPU performs control so that when the electro-pneumatic proportional valve starts flow rate adjustment, the electro-pneumatic proportional valve uses the adjustment value stored in the memory.

4. The pneumoperitoneum apparatus according to claim 2, wherein:
if the measured flow rate measured by the flow rate sensor decreases to or below the threshold value, the CPU performs control to stop operation of the electro-pneumatic proportional valve adjusting the insufflation flow rate, and
if the measured flow rate does not decrease to or below the threshold value, the CPU performs control to continue the operation of the electro-pneumatic proportional valve adjusting the insufflation flow rate.

5. The pneumoperitoneum apparatus according to claim 2, wherein the threshold value is an insufflation flow rate value that is at least larger than 0.

6. The pneumoperitoneum apparatus according to claim 2, further comprising:
a selection switch for selecting a detection operation from a plurality of detection operations for detecting a second switching via an insufflation button, the insufflation button being operated to make a first switching of the endoscope insufflation conduit provided in the endoscope from a closed state to an open state and make the second switching of the endoscope insufflation conduit from an open state to a closed state,
wherein:
if the CPU determines, according to the selection via the selection switch, that a predetermined condition including a first condition that the measured flow rate measured by the flow rate sensor decreases to or below the threshold value is met, the CPU performs control to stop operation of adjusting the insufflation flow rate via the electro-pneumatic proportional valve and set the adjustment value read from the memory, and
if the CPU determines that the predetermined condition is not met, the CPU performs control to continue the operation of adjusting the insufflation flow rate via the electro-pneumatic proportional valve.

7. The pneumoperitoneum apparatus according to claim 6, further comprising:
a pressure sensor that measures a pressure when the endoscope insufflation conduit is in a closed state,
wherein:
if a measured pressure value measured by the pressure sensor exceeds a pressure threshold value for detecting the pressure in the closed state, the CPU determines that the predetermined condition is met, and performs control to stop operation of the electro-pneumatic proportional valve adjusting the insufflation flow rate and performs control to set the adjustment value read from the memory, and
if the measured pressure value does not exceed the pressure threshold value for detecting the pressure in the closed state, the CPU performs control to continue the operation of the electro-pneumatic proportional valve adjusting the insufflation flow rate.

8. The pneumoperitoneum apparatus according to claim 2, wherein:
if the measured flow rate measured by the flow rate sensor decreases to or below the threshold value, the CPU further performs control to stop operation of the electro-pneumatic proportional valve adjusting the insufflation flow rate and performs control to set the adjustment value read from the memory, and performs control so that the electro-pneumatic proportional valve performs subsequent insufflation flow rate adjustment using the set adjustment value, and
if the measured flow rate does not decrease to or below the threshold value, the CPU performs control to continue the operation of the electro-pneumatic proportional valve adjusting the insufflation flow rate.

9. The pneumoperitoneum apparatus according to claim 2, wherein:
if the measured flow rate measured at a first time by the flow rate sensor decreases to or below a predetermined threshold value compared to a measured flow rate value measured at a second time immediately before the first time, the CPU performs control to stop operation of the electro-pneumatic proportional valve adjusting the insufflation flow rate, and
if the measured flow rate measured at the first time does not decrease to or below the predetermined threshold value, the CPU performs control to continue the operation of the electro-pneumatic proportional valve adjusting the insufflation flow rate.

10. The pneumoperitoneum apparatus according to claim 2, wherein:
if the measured flow rate measured by the flow rate sensor decreases to or below the threshold value that is set to 80% to 90% of the set flow rate after the measured flow rate reaches the set flow rate, the CPU performs control to stop operation of the electro-pneumatic proportional valve adjusting the insufflation flow rate, and
if the measured flow rate does not decrease to or below the threshold value that is set to 80% to 90% of the set flow rate after the measured flow rate reaches the set flow rate, the CPU performs control to continue the operation of the electro-pneumatic proportional valve adjusting the insufflation flow rate.

11. The pneumoperitoneum apparatus according to claim 2, further comprising:
a selection switch for selecting a detection mode from a plurality of detection modes for detecting switching of the endoscope insufflation conduit from an open state to a closed state via an insufflation button provided in the endoscope,
wherein the CPU performs control of operation according to the selection via the selection switch.

12. An endoscope system comprising:
the pneumoperitoneum apparatus according to claim 2; and
the endoscope including the endoscope insufflation conduit.

13. The endoscope system according to claim 12, wherein the endoscope includes a flexible insertion portion.

\* \* \* \* \*